United States Patent
Rosenberg et al.

(10) Patent No.: US 9,884,168 B2
(45) Date of Patent: *Feb. 6, 2018

(54) TEMPORARY RETENTION DEVICE

(71) Applicant: INTERRAD Medical, Inc., Plymouth, MN (US)

(72) Inventors: Michael S. Rosenberg, Eagan, MN (US); Timothy J. Claude, Coon Rapids, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/946,452

(22) Filed: Nov. 19, 2015

(65) Prior Publication Data

US 2016/0074629 A1 Mar. 17, 2016

Related U.S. Application Data

(63) Continuation of application No. 14/219,415, filed on Mar. 19, 2014, now Pat. No. 9,227,040, which is a continuation of application No. 13/552,081, filed on Jul. 18, 2012, now Pat. No. 8,715,295, which is a continuation of application No. 13/072,421, filed on
(Continued)

(51) Int. Cl.
*A61M 25/02* (2006.01)
*A61M 25/04* (2006.01)
*A61B 17/34* (2006.01)

(52) U.S. Cl.
CPC .......... *A61M 25/04* (2013.01); *A61B 17/3478* (2013.01); *A61B 2017/3484* (2013.01)

(58) Field of Classification Search
CPC .......... A61B 17/3415; A61B 2017/348; A61B 2017/3482; A61B 2017/3484; A61B 2017/3488; A61M 2025/0286; A61M 2025/0293; A61M 25/01; A61M 25/0194; A61M 25/02; A61M 25/04
See application file for complete search history.

(56) References Cited

U.S. PATENT DOCUMENTS 1,242,314 A 10/1917 Bean
1,380,447 A 6/1921 Wescott
(Continued)

FOREIGN PATENT DOCUMENTS

EP 0341039 11/1989
WO WO1991015254 10/1991
(Continued)

OTHER PUBLICATIONS

Johnson & Johnson web page printout, "The EndoANCHOR Comparative Summary" printed Sep. 13, 2005, 2 pages.
(Continued)

*Primary Examiner* — Ryan J Severson
(74) *Attorney, Agent, or Firm* — Fish & Richardson P.C.

(57) ABSTRACT

A retention device for anchoring indwelling catheters, sheath introducers, feeding tubes, ostomy bags or other medical devices beneath the skin of a patient includes an deployable section coupled to a medical device; following introduction into a patient, the deployable section is subcutaneously deployed, securely anchoring the device and coupled medical device for the duration of treatment.

17 Claims, 35 Drawing Sheets

Related U.S. Application Data

Mar. 25, 2011, now Pat. No. 8,252,004, which is a continuation of application No. 11/562,770, filed on Nov. 22, 2006, now Pat. No. 7,935,127, which is a continuation of application No. 11/085,016, filed on Mar. 18, 2005, now Pat. No. 7,931,658, which is a continuation-in-part of application No. PCT/US13/15144, filed on May 14, 2003, which is a continuation of application No. 10/383,903, filed on Mar. 7, 2003, now Pat. No. 6,695,861.

(60) Provisional application No. 60/412,453, filed on Sep. 20, 2002.

(56) References Cited

U.S. PATENT DOCUMENTS

| | | |
|---|---|---|
| 1,624,716 A | 4/1927 | Ferdinando |
| 1,998,225 A | 4/1935 | Frances |
| 2,525,398 A | 10/1950 | Collins |
| 3,039,468 A | 6/1962 | Price |
| 3,059,645 A | 10/1962 | Hasbrouck et al. |
| 3,108,595 A | 10/1963 | Overment |
| 3,176,690 A | 4/1965 | Doubler |
| 3,308,819 A | 3/1967 | Aip |
| 3,630,195 A | 12/1971 | Santomieri |
| 3,677,250 A | 7/1972 | Thomas |
| 3,717,151 A | 2/1973 | Collett |
| 3,765,032 A | 10/1973 | Palma |
| 3,777,761 A | 12/1973 | Sheridan |
| 3,825,010 A | 7/1974 | McDonald |
| 3,834,380 A | 9/1974 | Boyd |
| 3,856,009 A | 12/1974 | Winnie |
| 3,896,527 A | 7/1975 | Miller et al. |
| 3,902,501 A | 9/1975 | Citron et al. |
| 3,938,529 A | 2/1976 | Gibbons |
| 4,043,346 A | 8/1977 | Mobley et al. |
| 4,083,370 A | 4/1978 | Taylor |
| 4,114,618 A | 9/1978 | Vargas |
| 4,164,943 A | 8/1979 | Hill et al. |
| 4,230,110 A | 10/1980 | Beroff |
| 4,248,224 A | 2/1981 | Jones |
| 4,278,092 A | 7/1981 | Borsanyi et al. |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,279 A | 1/1991 | O'Neill |
| 4,986,810 A | 1/1991 | Semrad |
| 5,041,085 A | 8/1991 | Osborne et al. |
| 5,067,957 A | 11/1991 | Jervis |
| 5,088,979 A | 2/1992 | Filipi et al. |
| 5,122,122 A | 6/1992 | Allgood |
| 5,190,546 A | 3/1993 | Jervis |
| 5,253,643 A | 10/1993 | Price |
| 5,256,146 A | 10/1993 | Ensminger et al. |
| 5,257,975 A | 11/1993 | Foshee |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,353,787 A | 10/1994 | Price |
| 5,354,279 A | 10/1994 | Hofling |
| 5,368,017 A | 11/1994 | Sorenson et al. |
| 5,377,667 A | 1/1995 | Patton et al. |
| 5,378,239 A | 1/1995 | Termin et al. |
| 5,391,156 A | 2/1995 | Hildwein et al. |
| 5,419,777 A | 5/1995 | Hofling |
| 5,456,671 A | 10/1995 | Bierman |
| 5,470,321 A | 11/1995 | Forster et al. |
| 5,496,277 A | 3/1996 | Termin et al. |
| 5,531,676 A | 7/1996 | Edwards et al. |
| 5,540,648 A | 7/1996 | Yoon |
| 5,578,013 A | 11/1996 | Bierman |
| 5,597,378 A | 1/1997 | Jervis |
| 5,599,311 A | 2/1997 | Raulerson |
| 5,616,131 A | 4/1997 | Sauer et al. |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A * | 3/1998 | Kontos ............... A61B 17/0057 128/887 |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,792,115 A | 8/1998 | Horn |
| 5,800,402 A | 9/1998 | Bierman |
| 5,810,781 A | 9/1998 | Bierman |
| 5,814,065 A | 9/1998 | Diaz |
| 5,817,062 A | 10/1998 | Flom et al. |
| 5,827,230 A | 10/1998 | Bierman |
| 5,833,664 A | 11/1998 | Scare |
| 5,833,667 A | 11/1998 | Bierman |
| 5,857,999 A | 1/1999 | Quick et al. |
| 5,879,333 A | 3/1999 | Smith |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,984,896 A | 11/1999 | Boyd |
| 5,989,265 A | 11/1999 | Bouquet De La Joliniere et al. |
| 6,090,072 A | 7/2000 | Kratoska et al. |
| 6,213,979 B1 | 4/2001 | Bierman |
| 6,217,527 B1 * | 4/2001 | Selmon ............... A61B 17/3207 600/585 |
| 6,217,554 B1 | 4/2001 | Green |
| 6,231,548 B1 | 5/2001 | Bassett |
| 6,290,676 B1 | 9/2001 | Bierman |
| 6,413,240 B1 | 7/2002 | Bierman et al. |
| 6,447,485 B2 | 9/2002 | Bierman |
| 6,533,762 B2 | 3/2003 | Kanner et al. |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,638,234 B2 | 10/2003 | Burbank et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,786,892 B2 | 9/2004 | Bierman |
| 6,827,705 B2 | 12/2004 | Bierman |
| 6,837,875 B1 | 1/2005 | Bierman et al. |
| 6,896,665 B2 | 5/2005 | Picha et al. |
| 6,929,625 B2 | 8/2005 | Bierman |
| 6,958,044 B2 | 10/2005 | Burbank et al. |
| 6,972,003 B2 | 12/2005 | Bierman et al. |
| 7,018,362 B2 | 3/2006 | Bierman et al. |
| 7,056,286 B2 | 6/2006 | Ravenscroft et al. |
| 7,087,069 B2 | 8/2006 | Petrovic et al. |
| 7,247,150 B2 | 7/2007 | Bierman |
| 7,273,468 B2 | 9/2007 | Bedell |
| 7,377,910 B2 | 5/2008 | Katoh et al. |
| 7,753,889 B2 * | 7/2010 | Rosenberg ............ A61M 25/04 604/174 |
| 7,811,251 B2 | 10/2010 | Wenchell et al. |
| 7,931,658 B2 | 4/2011 | Rosenberg et al. |
| 7,935,127 B2 | 5/2011 | Rosenberg et al. |
| 8,016,794 B2 | 9/2011 | Rosenberg et al. |
| 8,016,813 B2 | 9/2011 | Rosenberg et al. |
| 8,038,653 B2 | 10/2011 | Rosenberg et al. |

(56) References Cited

U.S. PATENT DOCUMENTS

| | | | |
|---|---|---|---|
| 8,142,401 B2* | 3/2012 | Rosenberg | A61M 25/04 604/174 |
| 8,147,459 B2* | 4/2012 | Rosenberg | A61B 17/3415 604/164.01 |
| 8,235,948 B2 | 8/2012 | Rosenberg et al. | |
| 8,252,004 B2 | 8/2012 | Rosenberg et al. | |
| 8,328,764 B2 | 12/2012 | Rosenberg et al. | |
| 8,444,603 B2 | 5/2013 | Rosenberg et al. | |
| 8,579,864 B2 | 11/2013 | Rosenberg et al. | |
| 8,585,654 B2* | 11/2013 | Rosenberg | A61B 17/3415 604/164.01 |
| 8,628,511 B2* | 1/2014 | Rosenberg | A61M 25/02 604/506 |
| 8,715,295 B2* | 5/2014 | Rosenberg | A61M 25/04 606/108 |
| 8,771,232 B2 | 7/2014 | Rosenberg et al. | |
| 8,920,380 B2* | 12/2014 | Rosenberg | A61M 25/04 604/106 |
| 8,974,434 B2 | 3/2015 | Rosenberg et al. | |
| 8,986,257 B2 | 3/2015 | Rosenberg et al. | |
| 9,056,187 B2 | 6/2015 | Rosenberg et al. | |
| 9,227,040 B2 | 1/2016 | Rosenberg et al. | |
| 9,283,355 B2* | 3/2016 | Rosenberg | A61M 25/02 |
| 9,381,323 B2* | 7/2016 | Rosenberg | A61M 25/02 |
| 9,545,503 B2* | 1/2017 | Rosenberg | A61B 17/3415 |
| 2001/0056261 A1 | 12/2001 | Lerman et al. | |
| 2002/0068898 A1 | 6/2002 | McGucklin, Jr. et al. | |
| 2002/0068899 A1 | 6/2002 | McGucklin, Jr. et al. | |
| 2002/0120250 A1 | 8/2002 | Altman | |
| 2002/0165489 A1 | 11/2002 | McGucklin, Jr. et al. | |
| 2003/0040712 A1 | 2/2003 | Ray et al. | |
| 2004/0176726 A1 | 9/2004 | Katoh et al. | |
| 2005/0043685 A1 | 2/2005 | Schinkel-Fleitmann | |
| 2005/0137498 A1 | 6/2005 | Sakal et al. | |
| 2005/0187578 A1* | 8/2005 | Rosenberg | A61M 25/04 606/232 |
| 2005/0256458 A1 | 11/2005 | Howard et al. | |
| 2005/0256459 A1 | 11/2005 | Howard et al. | |
| 2005/0273058 A1 | 12/2005 | Bierman | |
| 2006/0079845 A1 | 4/2006 | Howard et al. | |
| 2007/0021685 A1 | 1/2007 | Oepen et al. | |
| 2007/0078397 A1 | 4/2007 | Weststrate | |
| 2007/0106330 A1* | 5/2007 | Rosenberg | A61M 25/04 606/232 |
| 2007/0225651 A1 | 9/2007 | Rosenberg et al. | |
| 2007/0232997 A1 | 10/2007 | Glenn | |
| 2008/0312599 A1 | 12/2008 | Rosenberg | |
| 2009/0054843 A1 | 2/2009 | Lundqvist | |
| 2009/0099527 A1 | 4/2009 | Rosenberg et al. | |
| 2009/0326470 A1* | 12/2009 | Rosenberg | A61M 25/02 604/175 |
| 2009/0326473 A1 | 12/2009 | Rosenberg et al. | |
| 2010/0016801 A1 | 1/2010 | Rosenberg et al. | |
| 2010/0241084 A1* | 9/2010 | Rosenberg | A61M 25/04 604/175 |
| 2011/0172607 A1* | 7/2011 | Rosenberg | A61M 25/04 604/175 |
| 2011/0301543 A1* | 12/2011 | Rosenberg | A61M 25/02 604/175 |
| 2012/0004617 A1 | 1/2012 | Rosenberg et al. | |
| 2012/0157925 A1* | 6/2012 | Rosenberg | A61B 17/3415 604/175 |
| 2012/0157926 A1* | 6/2012 | Rosenberg | A61M 25/04 604/175 |
| 2012/0271238 A1* | 10/2012 | Rosenberg | A61M 25/02 604/175 |
| 2012/0283644 A1* | 11/2012 | Rosenberg | A61M 25/04 604/175 |
| 2014/0046264 A1* | 2/2014 | Rosenberg | A61B 17/3415 604/175 |
| 2014/0107583 A1* | 4/2014 | Rosenberg | A61M 25/02 604/174 |
| 2014/0207147 A1* | 7/2014 | Rosenberg | A61M 25/04 606/108 |
| 2014/0276438 A1 | 9/2014 | Rosenberg | |
| 2015/0080804 A1* | 3/2015 | Rosenberg | A61M 25/04 604/175 |
| 2015/0174373 A1 | 6/2015 | Rosenberg | |
| 2015/0246208 A1 | 9/2015 | Rosenberg | |
| 2016/0074629 A1* | 3/2016 | Rosenberg | A61M 25/04 604/174 |
| 2016/0151609 A1* | 6/2016 | Rosenberg | A61M 25/02 604/174 |
| 2016/0279389 A1* | 9/2016 | Rosenberg | A61M 25/02 |
| 2017/0216563 A1 | 8/2017 | Rosenberg et al. | |

FOREIGN PATENT DOCUMENTS

| | | |
|---|---|---|
| WO | WO2004026152 | 4/2004 |
| WO | WO2005039419 | 5/2005 |
| WO | WO2005102438 | 11/2005 |
| WO | WO2007082333 | 7/2007 |
| WO | WO2007103999 | 9/2007 |
| WO | WO2008051810 | 5/2008 |

OTHER PUBLICATIONS

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Web Page Printout of Statlock Device, believed to be publicly available prior to Jul. 2005, 2 pages.

* cited by examiner

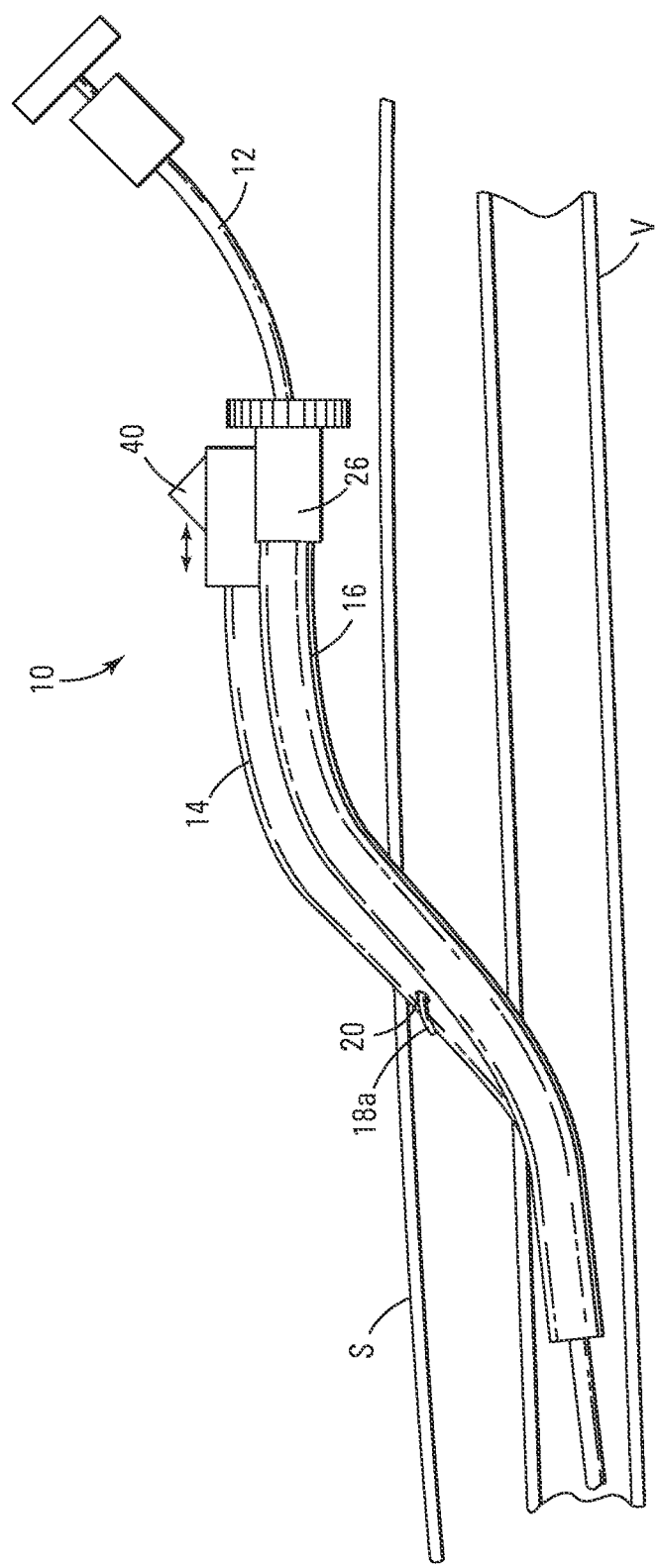

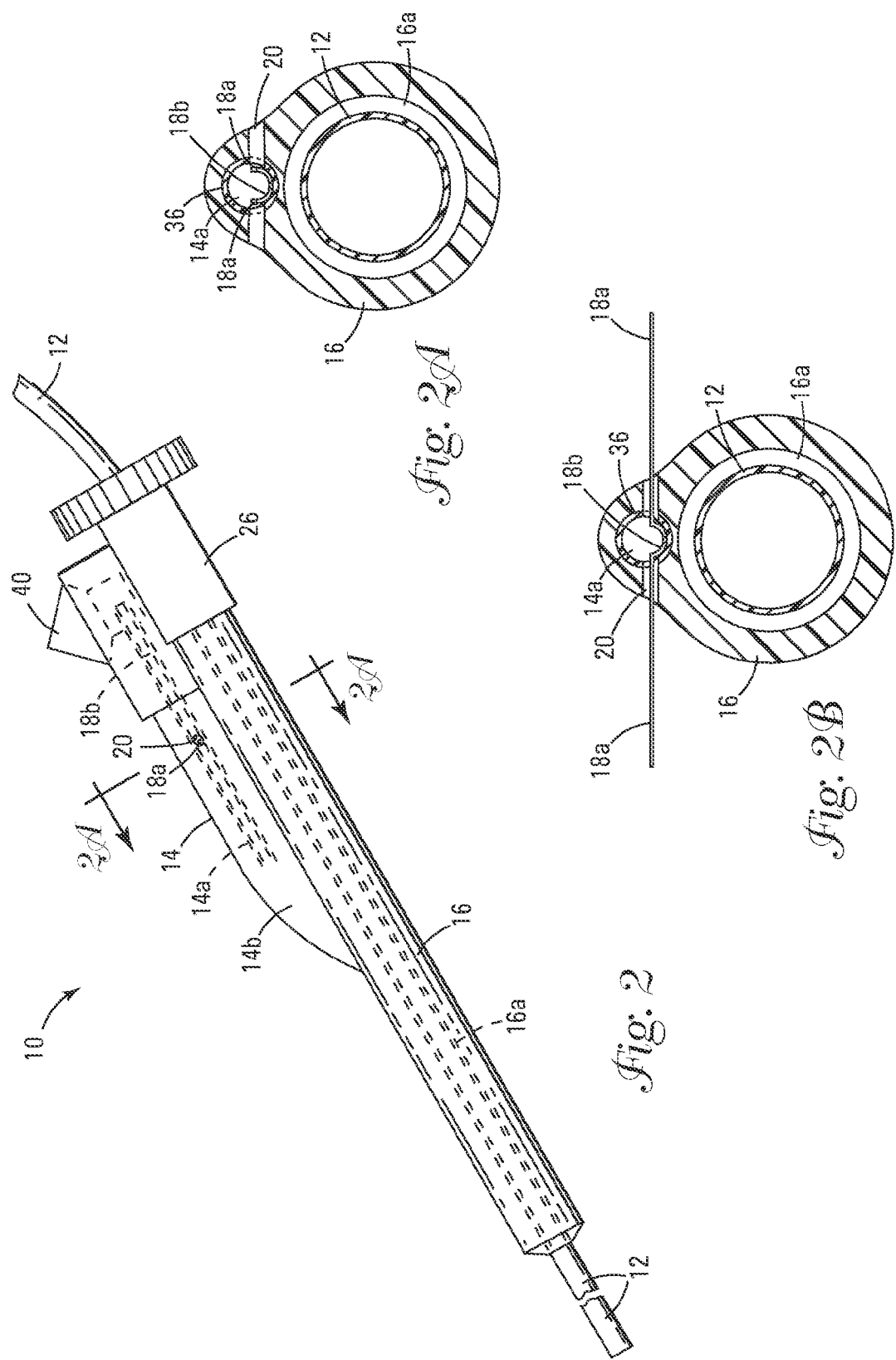

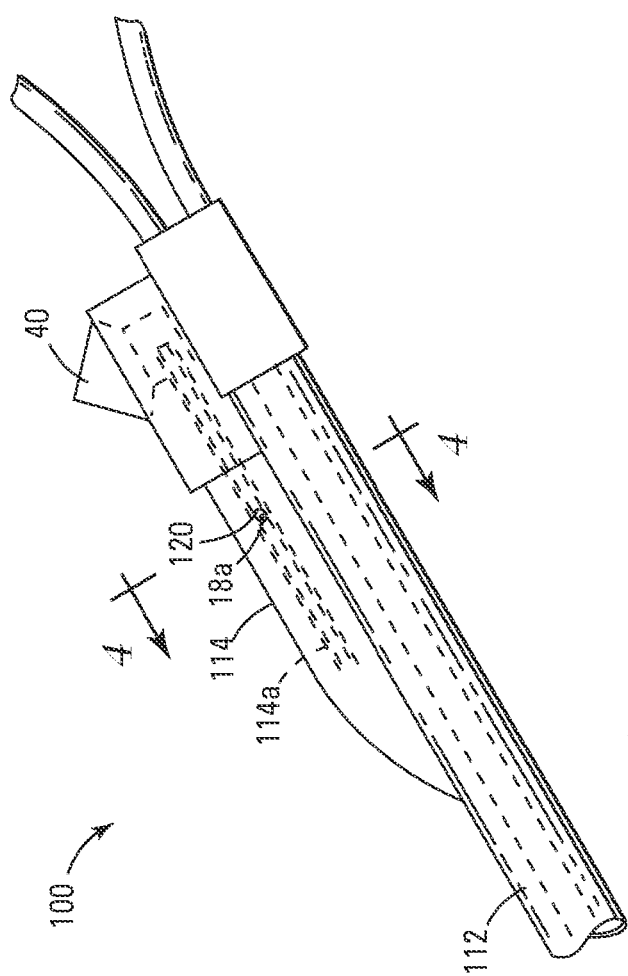
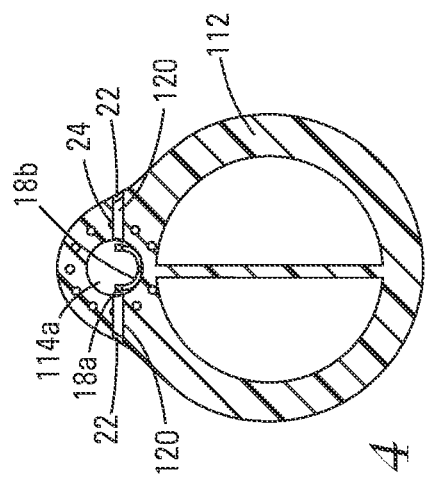

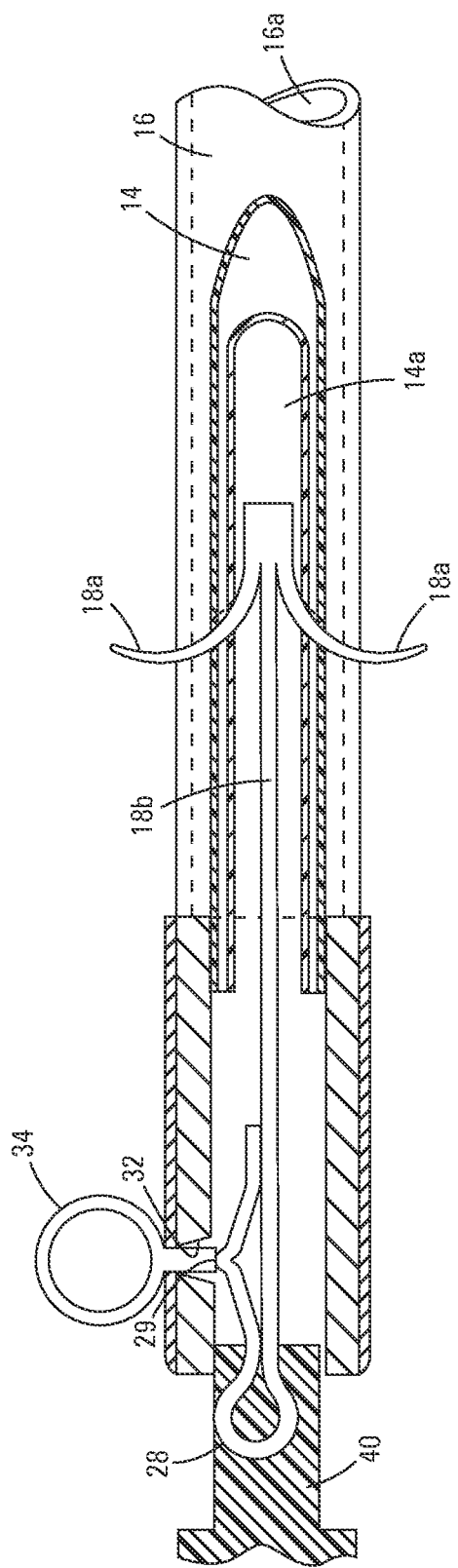

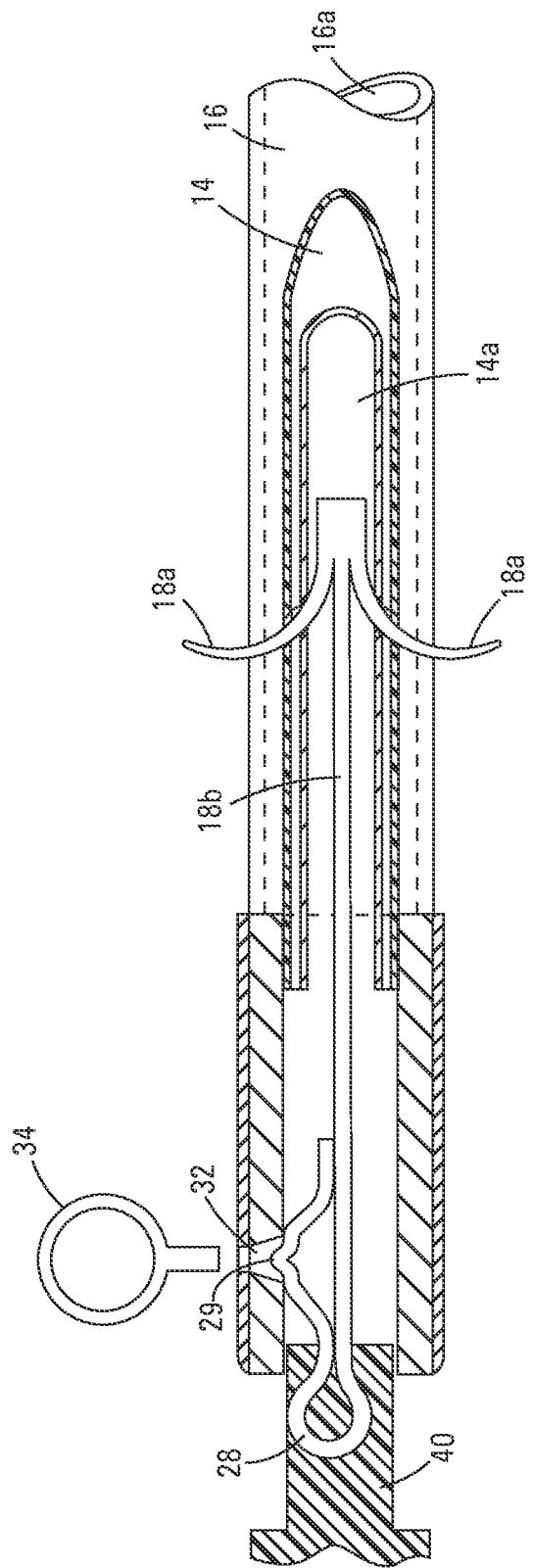

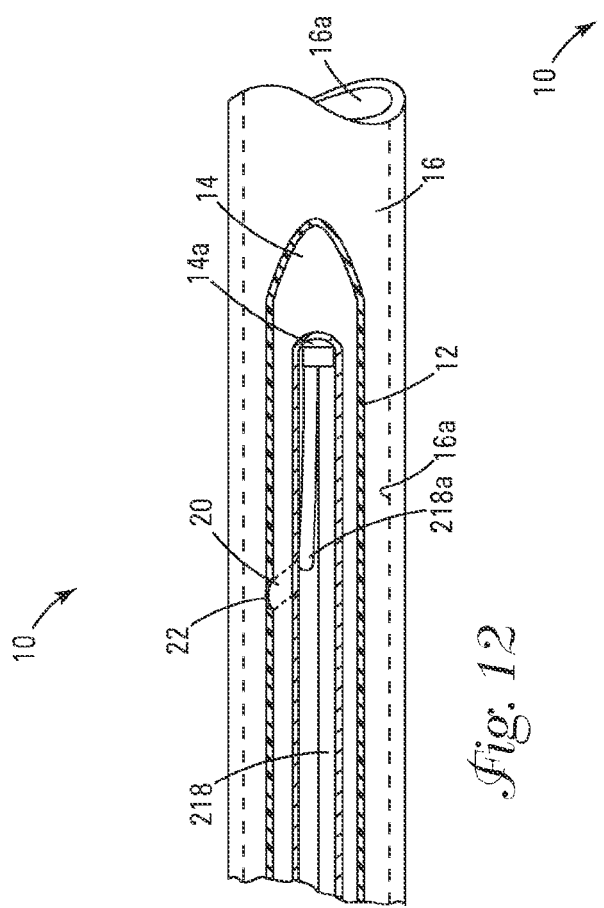
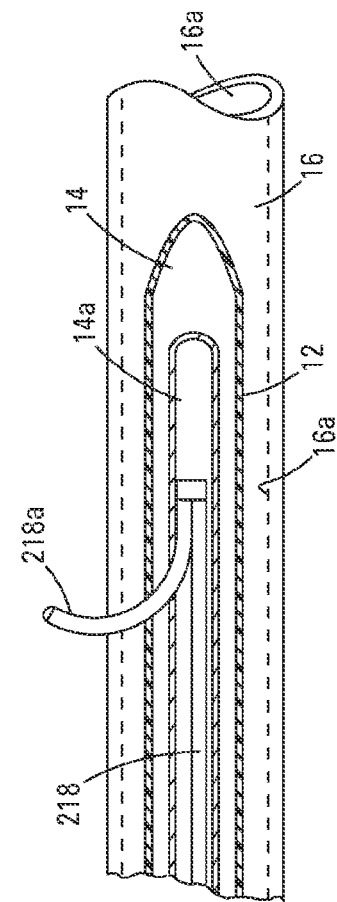
Fig. 12
Fig. 13

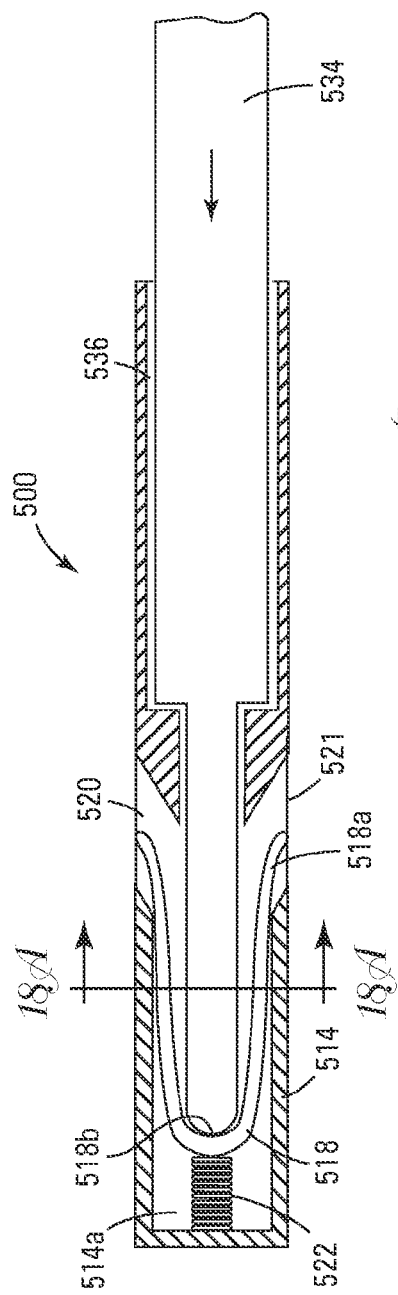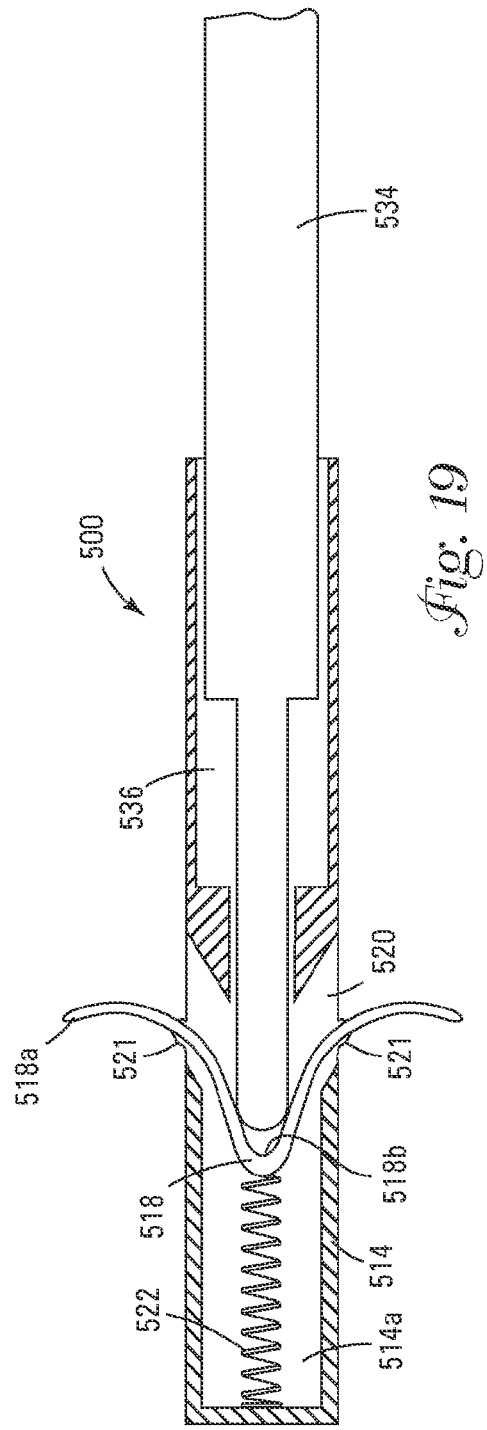

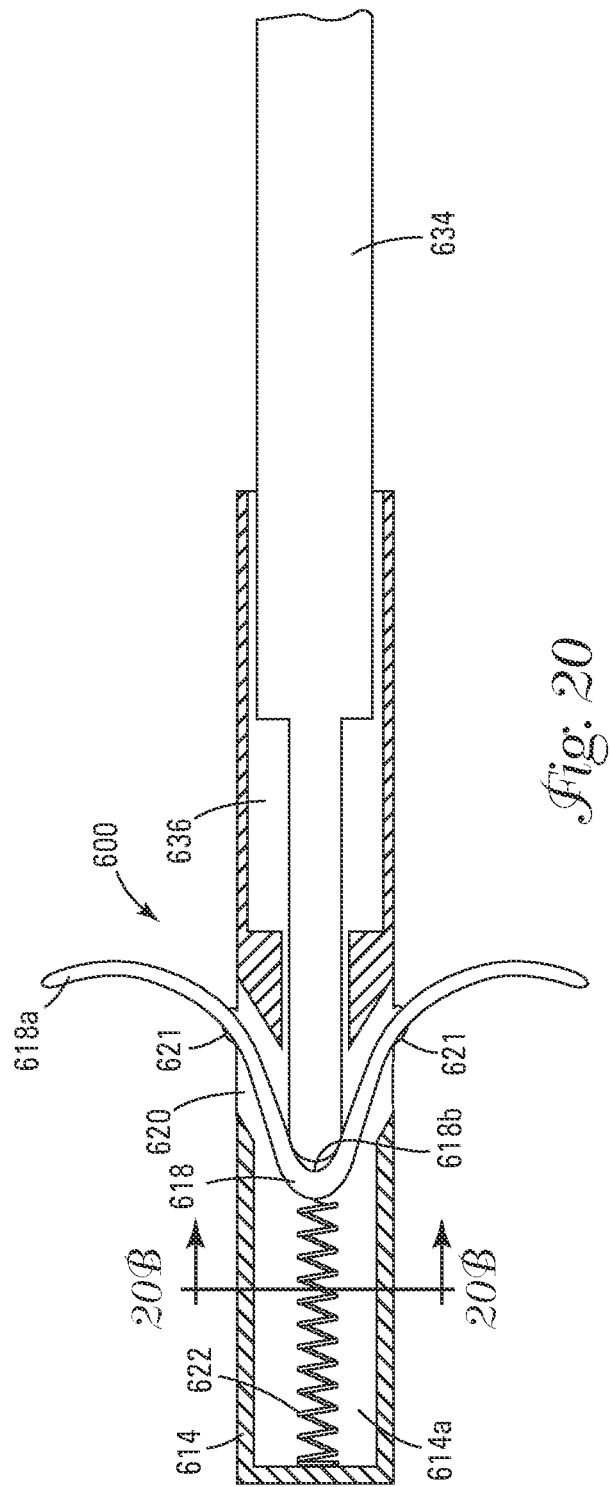

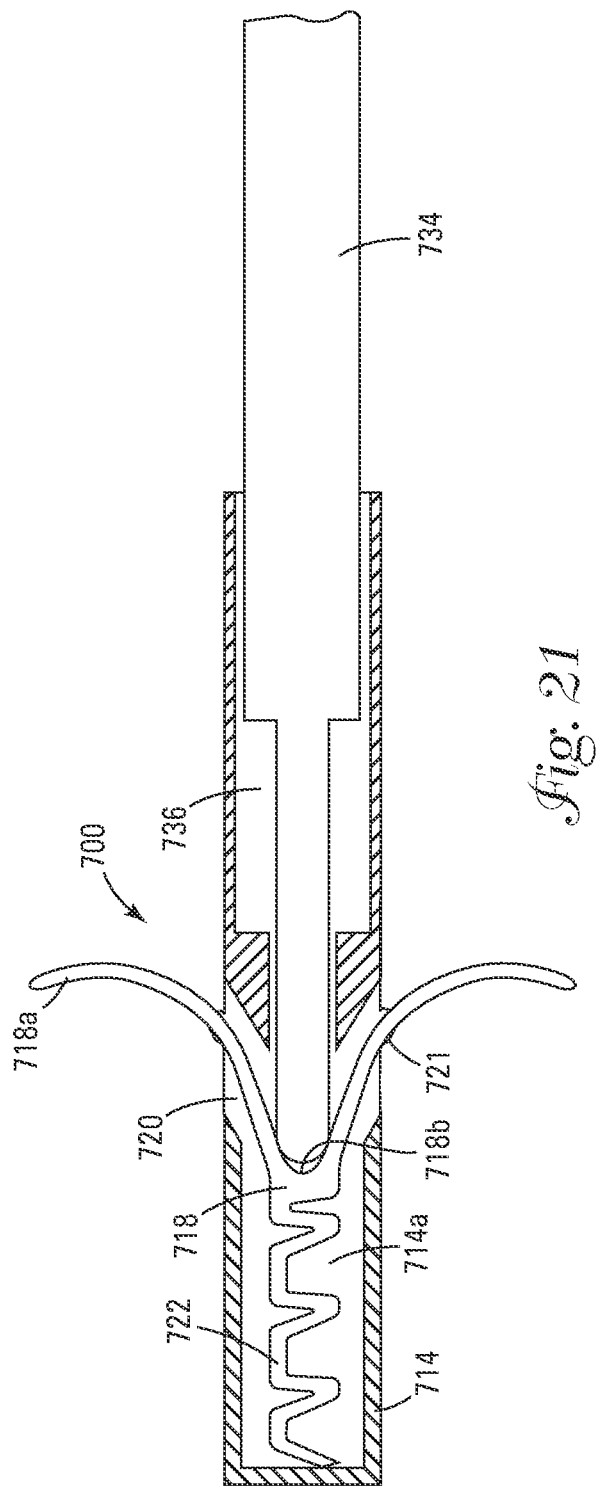

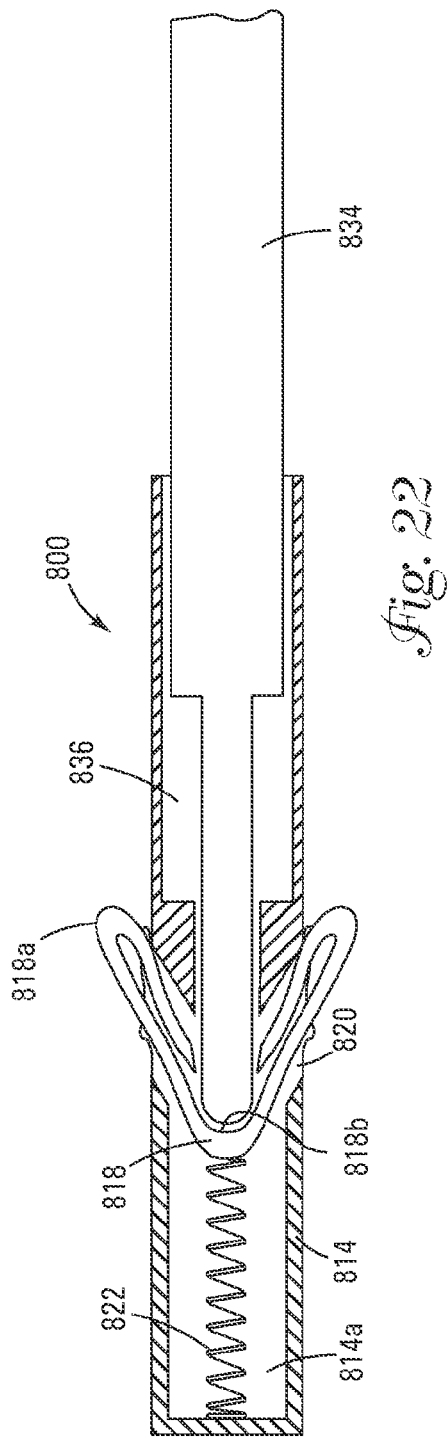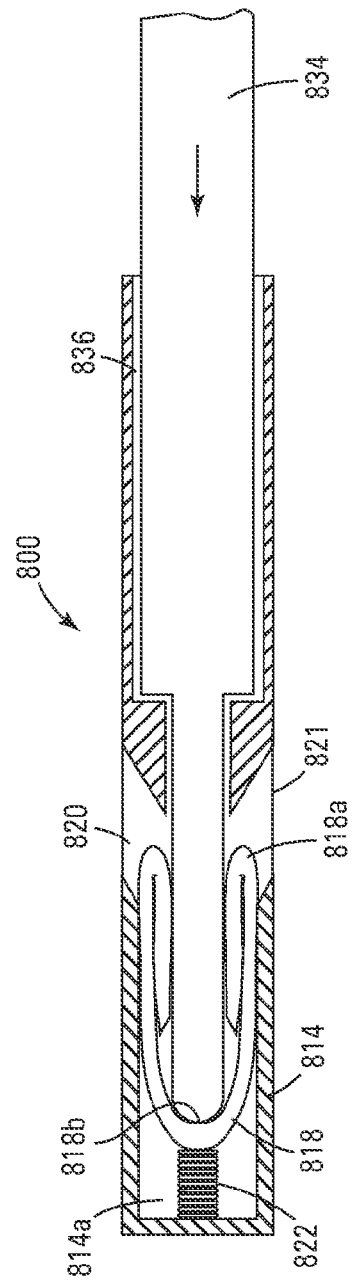

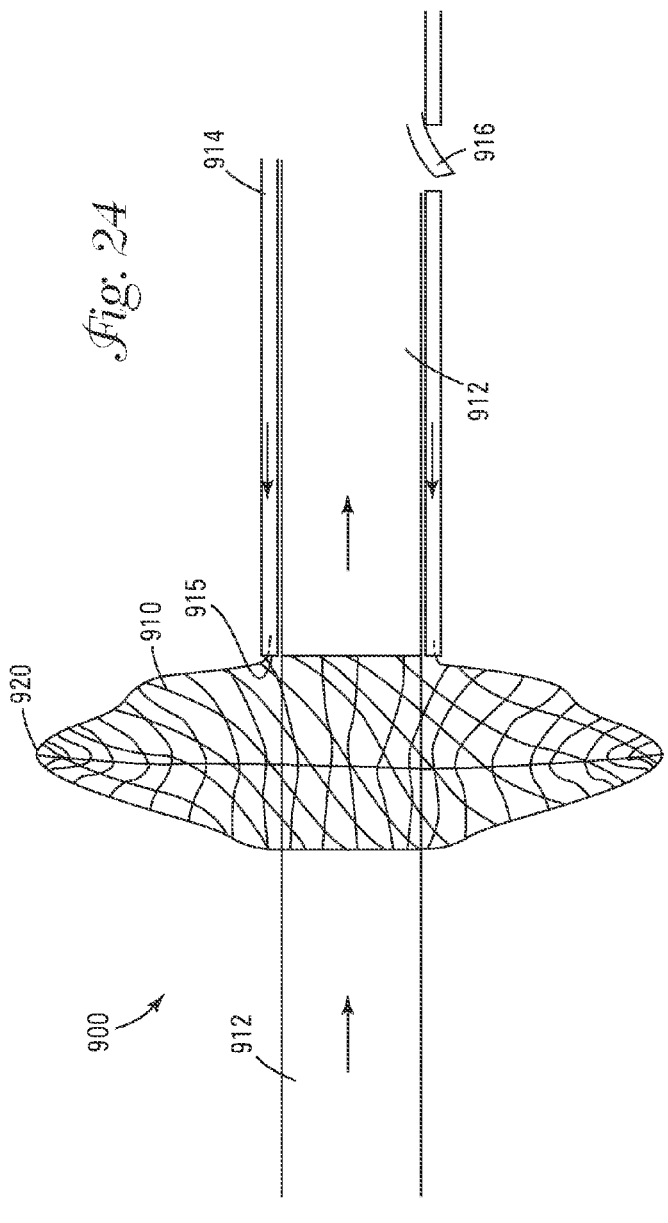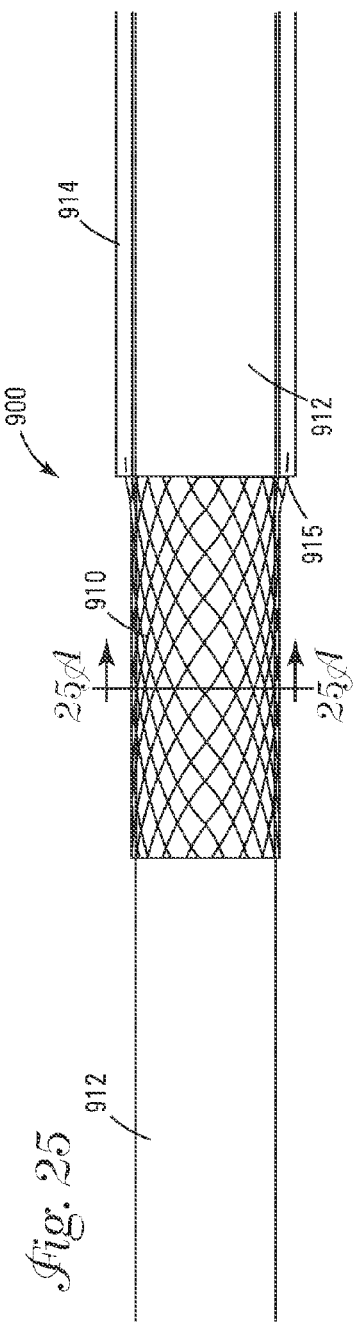

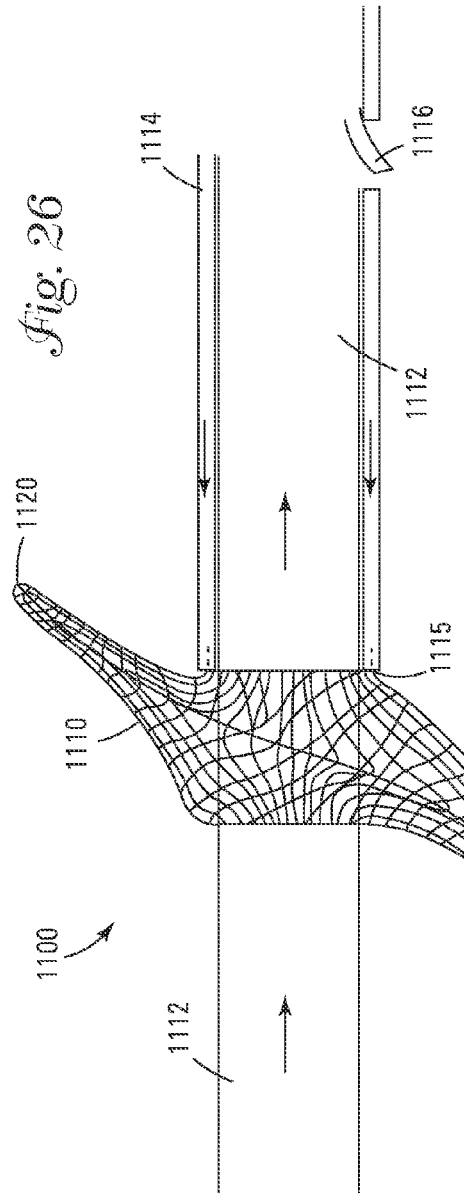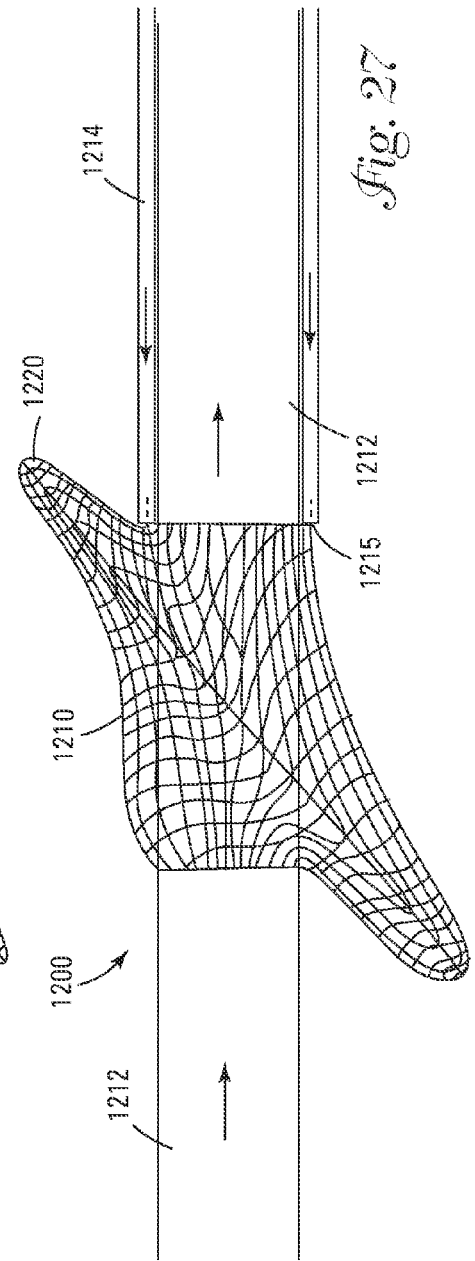

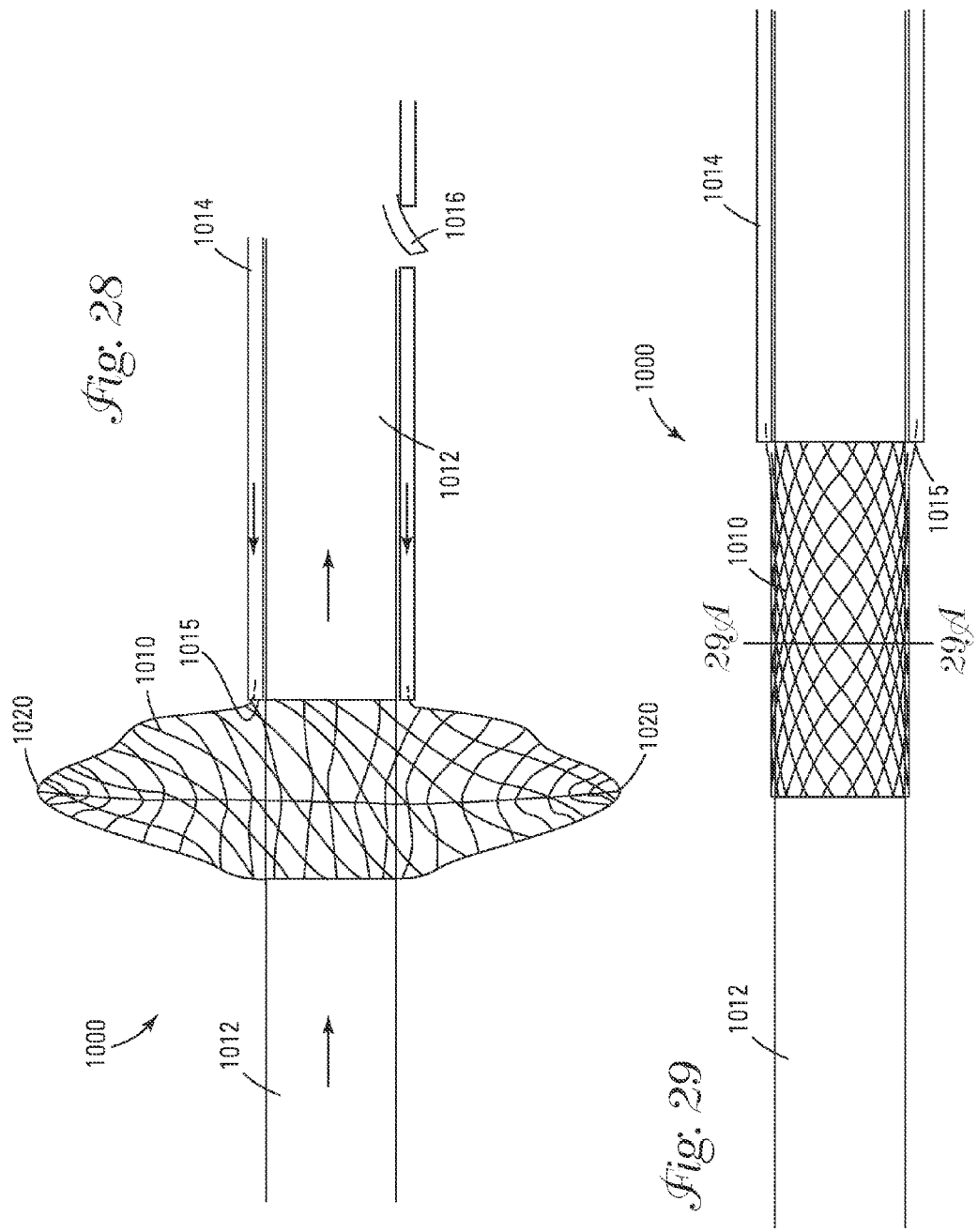

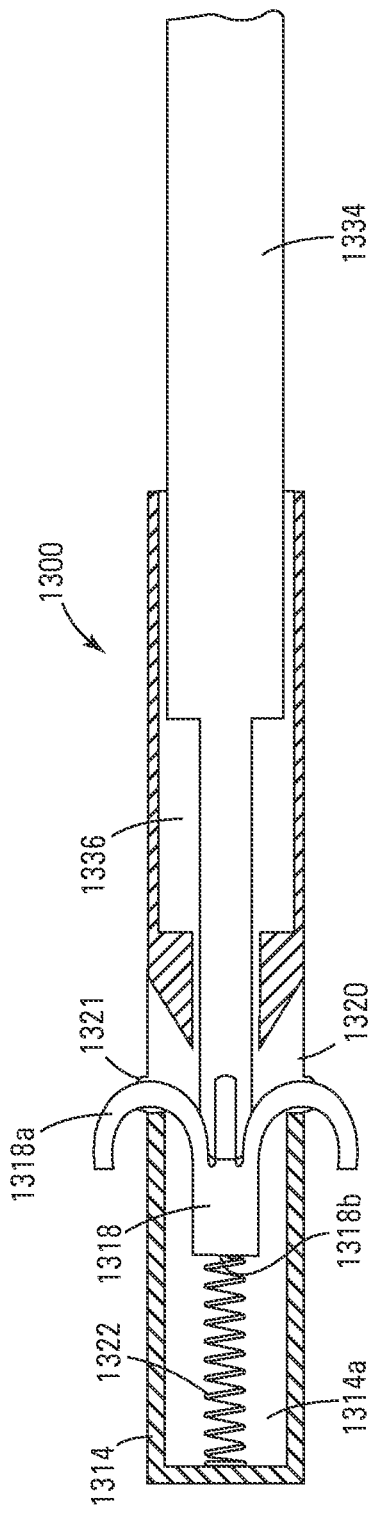
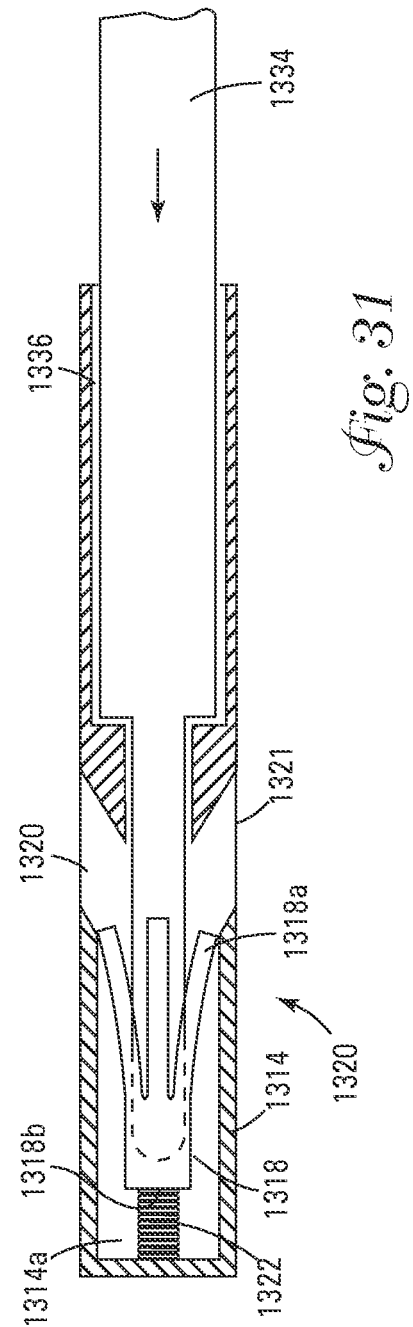

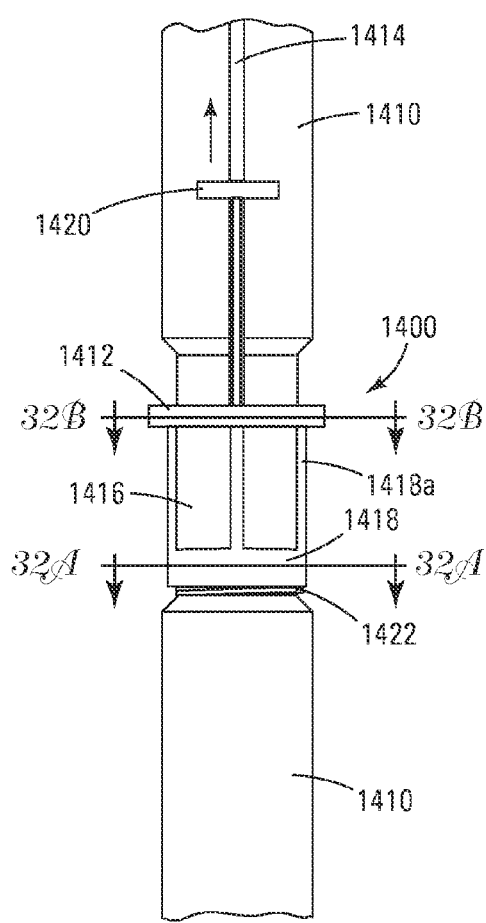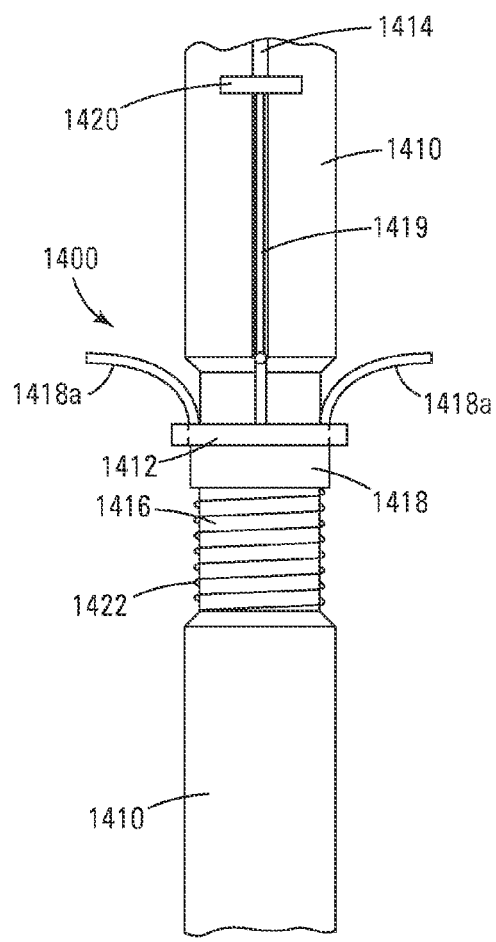

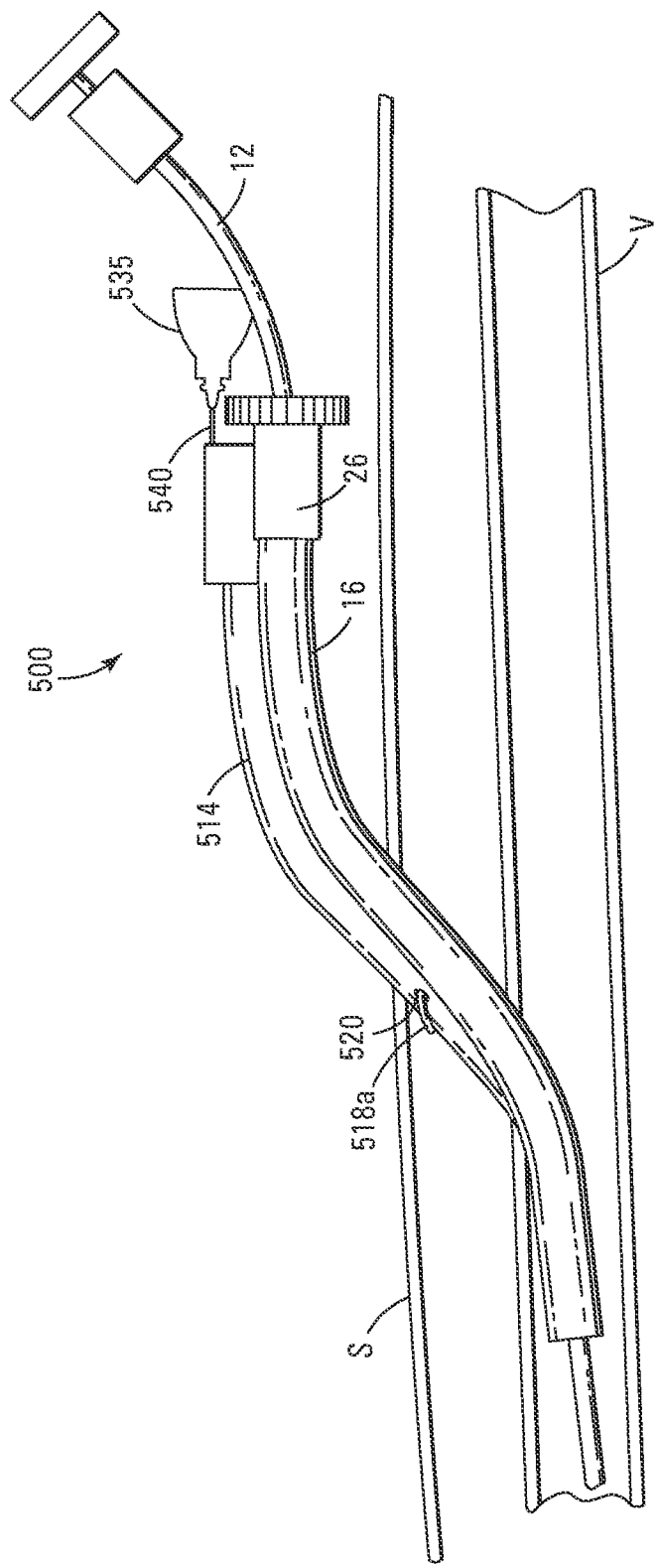

TEMPORARY RETENTION DEVICE

CROSS-REFERENCE TO RELATED APPLICATIONS

This application is a continuation of U.S. patent application Ser. No. 14/219,415 filed Mar. 19, 2014 (now U.S. Pat. No. 9,227,040), which is a continuation of U.S. patent application Ser. No. 13/552,081 filed on Jul. 18, 2012 by Rosenberg et al. (now U.S. Pat. No. 8,715,295), which is a continuation of U.S. patent application Ser. No. 13/072,421 filed on Mar. 25, 2011 by Rosenberg et al. (now U.S. Pat. No. 8,252,004), which is a continuation of U.S. patent application Ser. No. 11/562,770 filed on Nov. 22, 2006 by Rosenberg et al. (now U.S. Pat. No. 7,935,127), which is a continuation of U.S. patent application Ser. No. 11/085,016 filed on Mar. 18, 2005 by Rosenberg et al. (now U.S. Pat. No. 7,931,658), which is a continuation-in-part of and claims the benefit of International Patent Application PCT/US03/15144 filed May 14, 2003 (PCT Pub. No. WO 2004/026152), which is a continuation of and claims priority to U.S. patent application Ser. No. 10/383,903 filed on Mar. 7, 2003 by Rosenberg et al. (now U.S. Pat. No. 6,695,861), which claims priority to U.S. Provisional Patent Application Ser. No. 60/412,453 filed on Sep. 20, 2002, all of which are herein incorporated in their entirety.

FIELD OF THE INVENTION

The invention relates to a device for securing in-dwelling catheters, sheath introducers, feeding tubes, ostomy bags, pacing leads or other medical devices to patients.

BACKGROUND

Medical treatments requiring the delivery or drainage of various solutions such as antibiotics, cancer drug therapy, blood draws, abscessed biliary material or urinary tract fluids, rely upon a medical device such as indwelling catheters or sheath introducers to be inserted into the patient for an extended period of time such as thirty or even sixty or ninety days at a time. Additional procedures requiring other medical device such as feeding tubes, ostomy bags, or pacing leads similarly require introduction and continued placement for extended periods. A requirement for maintaining the medical device within a patient for such a period is that the medical device be secured so as not to move excessively during treatment.

Typically the physician creates an incision or puncture through the patient's skin with the goal of reaching an artery, vein, other vessel or anatomical site to allow insertion of the medical device at a specific anatomical site. Currently many temporarily implanted medical devices are secured utilizing a tab or eyelet formed in the medical device through which a suture is taken through the tab and skin. A standard 2-0 suture is most often used for this purpose, which is tied off thus securing the catheter within the patient's body. Suturing such a device to a patient, however, presents several problems: (1) Suturing a medical device to a patient's body makes it difficult to clean and disinfect the area around the insertion point, resulting in a high rate of infection in the area close to the device's insertion; (2) The medical device is subject to being dislodged from the patient following introduction resulting in migration of the medical device during treatment; and (3) A sutured medical device is subject to a disoriented patient ripping the medical device loose and tearing the suture out. This can result in patient injury and often necessitates costly replacement or additional corrective procedures.

An additional disadvantage of suturing a medical device to a patient is pain and discomfort to the patient during the period of treatment, as a result of a long-term suture extending through the patient's skin. Further, different physicians use different suturing and knotting techniques, resulting in a wide variation of pull strengths required to rip out and dislodge the sutured medical device from the patient's body.

Another securement method utilizes adhesive tape. In this method a layer of tape is placed over a cleaned external site on the patient's body after medical device insertion has been accomplished. The medical device is adhered to the skin by adhesive friction. This method is ineffective at reducing the incidence of infection. Further, it does not prevent the inadvertent and sometimes violent removal of the medical device prior to completion of treatment.

What is therefore needed is a retention device for medical devices that allows for simple and effective anchoring to the patient's body and also reduces the incidence of infection, migration and dislodgment.

SUMMARY

In one aspect the retention device comprises a device for subcutaneously anchoring a coupled medical device within a patient. The device has a distal section and a proximal section with a deployable section attached proximate the proximal section. When the device is introduced the deployable section when deployed deploys subcutaneously in a controllable manner. In another embodiment the device has the deployable section attached to a platform with the deployable section capable of transitioning between a first configuration proximate the platform and a second configuration extending from the platform.

In another aspect the retention device comprises a device for subcutaneously anchoring a coupled medical device within a patient and has a restraint and an anchor mechanism contacting the restraint. At least a portion of the anchor mechanism is capable of transitioning between a first configuration when restrained by the restraint and a second configuration when unrestrained by the restraint. The anchor mechanism has at least a single extension and at least a portion of the extension is capable of flexibly and repeatedly moving between the first configuration and the second configuration. The device defines a distal section and a proximal section, with the restraint and anchor mechanism proximate the proximal section. Separating the anchor mechanism and the restraint from each other unrestrains the extension in a gradual and controlled manner, thus causing the extension to gently transition from the first configuration toward the second configuration. In one embodiment the restraint is fixed and the anchor mechanism is movable so that at least a portion of the extension of the anchor mechanism can move toward the unrestrained second configuration. In an alternative embodiment, the anchor mechanism is fixed and the restraint is capable of moving to allow at least a portion of the extension of the anchor mechanism to move toward the unrestrained second configuration.

In yet another aspect, the retention device comprises a device for subcutaneously anchoring a coupled medical device within a patient. The device has an anchor sleeve with a chamber defining at least a single port. An anchor mechanism is movably loaded into the chamber, with the anchor mechanism capable of moving between a restrained first configuration and an unrestrained second configuration. The anchor mechanism has at least a single tine having a first end and a second free end, and the second end of the tine is capable of flexibly and repeatedly moving between the first configuration and the second configuration. The tine has a trained shape when in the second configuration, with the length of the tine such that the tine is restrained within the chamber when the anchor mechanism is in the first configuration. The port is sized and located so the free end of the tine is proximate the port when the tine is in the first configuration. Biasing means are provided to move the anchor mechanism into the second configuration. A removable actuation key is sized to fit into the anchor sleeve to contact the anchor mechanism. When the key is inserted into the anchor sleeve the anchor mechanism moves from the second configuration and is retained in the first configuration which causes the second end of the tine to enter the chamber through the port.

In still another aspect, the retention device comprises a device for subcutaneously anchoring a coupled medical device within a patient. The device has an anchor sleeve with a chamber defining a longitudinal axis and at least a single port. An anchor mechanism is movably loaded into the chamber, with the anchor mechanism capable of moving between a restrained first configuration and an unrestrained second configuration. The anchor mechanism has at least a single loop capable of extending from the port and the loop is capable of repeatedly moving between the first configuration and the second configuration. The loop has a trained shape when in the second configuration. Biasing means are provided to move the anchor mechanism into the second configuration. A key is sized to fit into the anchor sleeve to contact the anchor mechanism, where inserting the key into the anchor sleeve moves the anchor mechanism from the second configuration to the first configuration causing the loop to enter the chamber through the port.

In an alternative aspect the retention device comprises a device for subcutaneously anchoring a coupled medical device within a patient. The device has an inner sheath defining an outer dimension and an outer sheath defining an inner dimension, with the outer dimension of the inner sheath sized to slidably fit inside the inner dimension of the outer sheath. The outer sheath defines a sliding end, with the sliding end being movable along the inner sheath. A braid defines a length and a width, with the braid being attached at a first point to the sliding end of the outer sheath and at a second point to the inner sheath. The braid is capable of moving between an elongated configuration having a greater length and a lesser width and a shortened configuration having an inverse relationship between length and width. When the sliding end of the outer sheath is moved the full distance of its travel from the point of braid attachment on the inner sheath, the braid assumes the elongated configuration and the device can be introduced or removed from the patient. When the sliding end of the outer sheath is moved in a direction toward the point of braid attachment on the inner sheath, the braid moves toward the shortened configuration and the braid defines a widest circumference. In a further embodiment, the braid is coated with an elastomeric coating.

BRIEF DESCRIPTION OF THE DRAWINGS

In the drawings, identical reference numerals indicate identical or equivalent structure where:

FIG. 1 is a side view of an embodiment of the retention device following insertion through a patient's skin.

FIG. 2 is a side view of an embodiment of the invention with an anchor sleeve and anchor mechanism attached to an introducer sheath capable of receiving and securing a catheter, prior to the tine being deployed.

FIG. 2a is a cross sectional view taken through the lines 2a-2a of the embodiment of the invention shown in FIG. 2, with the anchor mechanism loaded into the anchor sleeve, prior to deployment.

FIG. 2b is a cross sectional view taken through the lines 2a-2a of the embodiment of the invention shown in FIG. 2 with the anchor mechanism loaded into and deployed from the anchor sleeve.

FIG. 3 is a side view of an embodiment of the invention with the anchor sleeve and anchor mechanism attached to a dual lumen catheter body and hub.

FIG. 4 is a cross sectional view taken between points 4-4 of the apparatus shown in FIG. 3.

FIG. 6a is a side view of an embodiment of the anchor mechanism.

FIG. 7 is a proximal end view of the embodiment of the anchor mechanism shown in FIG. 6a.

FIG. 10a is a cut away view of an embodiment of the retention device showing the lock mechanism following deployment of the tines and the key inserted prior to unlocking the lock mechanism.

FIG. 11 is a cut away view of an embodiment of the retention device showing the lock mechanism following deployment of the tines with the key removed from the recess.

FIG. 12 is a partial cut away view of an embodiment of the anchor mechanism loaded into the embodiment of the retention device shown in FIG. 2 prior to deployment of the tine.

FIG. 13 is a partial cut away view of an embodiment of the anchor mechanism loaded into the embodiment of the retention device shown in FIG. 2 following deployment of the tine.

FIG. 18 is a cut away side view of an embodiment of the retention device showing a separate spring and the anchor mechanism in the undeployed configuration.

FIG. 18a shows a cross section of the embodiment of the retention device shown in FIG. 18 taken through points 18a-18a.

FIG. 19 is a cut away side view of the embodiment of the retention device shown in FIG. 18 in the deployed configuration.

FIG. 20 is a cut away side view of an embodiment of the retention device similar to the device shown in FIG. 18, but showing an attached spring.

FIG. 21 is a cut away side view of an embodiment of the retention device similar to the device shown in FIG. 18 showing a spring integrally attached to the anchor mechanism.

FIG. 22 is a cut away side view of an embodiment of the retention device in the deployed configuration.

FIG. 23 is a cut away side view of the embodiment of the retention device shown in FIG. 22 in the undeployed configuration.

FIG. 24 is a partial cut away side view of an embodiment of the retention device in the deployed configuration, with the coated braid in the shortened symmetrical configuration.

FIG. 25 is a partial cut away side view of the embodiment of the retention device shown in FIG. 24 in the undeployed configuration, with the coated braid in the elongated configuration.

FIG. 26 is a partial cut away side view of an embodiment of the retention device in the deployed configuration, with the braid in the shortened 45 degree/45 degree asymmetrical configuration.

FIG. 27 is a partial cut away side view of an embodiment of the retention device in the deployed configuration, with the braid in the shortened 60 degree/30 degree asymmetrical configuration.

FIG. 28 is a partial cut away side view of an embodiment of the retention device in the deployed configuration, with the uncoated braid in the shortened 90 degree symmetrical configuration.

FIG. 29 is a partial cut away side view of the embodiment of the retention device shown in FIG. 28 in the undeployed configuration, with the uncoated braid in the elongated configuration.

FIG. 30 is a cut away side view of an embodiment of the retention device having an anchor mechanism made from cut tubing in the deployed configuration.

FIG. 31 is a cut away side view of an embodiment of the retention device shown in FIG. 30 in the undeployed configuration.

FIG. 32 is a side view of an embodiment of the retention device having a movable, externally mounted anchor mechanism in the undeployed configuration.

FIG. 32a shows a cross section of the embodiment shown in FIG. 32 taken through the lines 32a-32a.

FIG. 33 is a side view of the embodiment shown in FIG. 32 in the deployed configuration.

FIG. 36 is a side view of the embodiment of the retention device shown in FIGS. 18-19b attached to a sheath introducer following introduction and subcutaneous deployment.

DETAILED DESCRIPTION

Definitions

Figure 5:
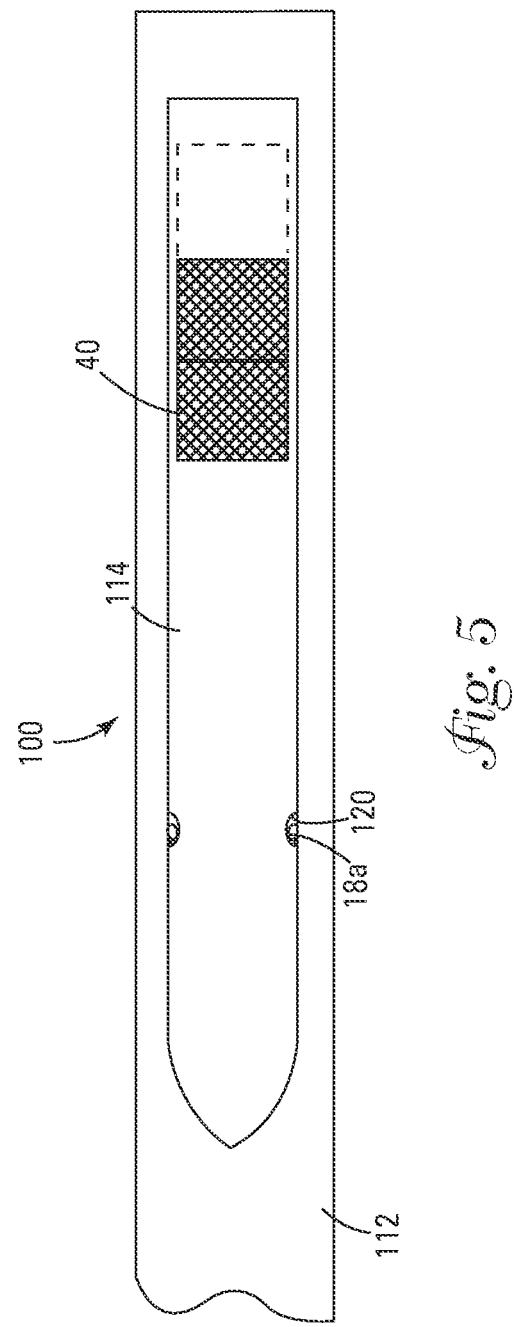
FIG. 5 is a top view of the embodiment of the invention shown in FIG. 3.

"Braid" refers to a structure made of interwoven strands.

"Catheter" is used in its generic sense and refers to any surgical instrument used to deliver a surgical device or chemical substance to a particular location in to the interior of a patient's body.

"Coil" refers to a structure made of a series of rings or spirals.

"Distal Section" refers to a location on a retention device and coupled medical device most distant from the operator.

"Elastomeric Polymeric Coating" refers to a polymeric coating based on silicone or urethane that is able to repeatedly be stretched and contracted without breaking or cracking.

"Longitudinal" refers to a lengthwise dimension.

"Loop" refers to a structure which may be open or closed and where open has the free end covered to prevent trauma to the patient.

"Medical Device" refers to any device used for medical, veterinary or dental treatment requiring temporary or permanent placement.

"Platform" is used in its generic sense and refers to a first structure to which a retention device is mounted, where the first structure is coupled to an underlying second structure.

"Port" refers to an opening or a thinning in a wall.

"Proximal Section" refers to a location on a retention device and coupled medical device closest to the operator and sufficiently inward to allow the retention device to deploy subcutaneously.

"PTFE" refers to polytetrafluoroethylene.

"Subcutaneous" refers to the anatomical area between the skin and dermal layers and underlying muscle tissue.

"Vessel" refers to any anatomical structure that connects organs within a body or outside the body. Examples include but are not limited to arteries, veins, bile duct, ureter, urethra, esophagus or other body conduits.

NOMENCLATURE

10 Retention Device
12 Catheter

14 Anchor Sleeve
14a Chamber
14b Floor of Anchor Sleeve
16 Introducer Sheath
16a Second Lumen
18 Anchor Mechanism
18a Tine
18b Control Rod
20 Port
22 Membrane
24 Braid
26 Hemostasis Valve
28 Eyelet
29 Lock Spring
32 Recess
34 Key
36 Liner
40 Handle
100 Retention Device
112 Catheter
114 Anchor Sleeve
114a Chamber
118 Anchor Mechanism
118a Tine
118b Control Rod
120 Port
128 Eyelet
129 Lock Spring
130 Weld
218 Anchor mechanism
218a Tine
218b Control Rod
228 Eyelet
229 Lock Spring
230 Weld
400 Retention Device
412 Catheter
414 Anchor Sleeve
414a Chamber
418 Anchor Mechanism
418a Tine
418b Control Rod
420 Port
428 Eyelet
429 Lock Spring
432 Recess
440 Handle
500 Retention Device
514 Anchor Sleeve
514a Chamber
518 Anchor Mechanism
518a Tine
518b Inner End
520 Port
521 Membrane
522 Spring
524 Reinforcing Braid
534 Key
535 Handle
536 Key Aperture
538 Locking Stop
540 Shaft
542 Locking Recess
600 Retention Device
614 Anchor Sleeve
614a Chamber
618 Anchor Mechanism
618a Tine
618b Inner End
620 Port
621 Membrane
622 Spring (Attached)
634 Key
636 Key Aperture
638 Liner
700 Retention Device
714 Anchor Sleeve
714a Chamber
718 Anchor Mechanism
718a Tine
718b Inner End
720 Port
721 Membrane
722 Spring (Integrally Attached to Anchor Mechanism)
734 Key
736 Key Aperture
800 Retention Device
814 Anchor Sleeve
814a Chamber
818 Anchor Mechanism
818a Loop
818b Inner End
820 Port
821 Membrane
822 Spring
834 Key
836 Key Aperture
900 Retention Device
910 Braid
912 Inner Sheath
913 Lumen
914 Outer Sheath
915 Sliding End
916 Locking Tab
918 Coating
920 Widest Circumference
1000 Retention Device
1010 Braid
1012 Inner Sheath
1013 Lumen
1014 Outer Sheath
1015 Sliding End
1016 Locking Tab
1020 Widest Circumference
1100 Retention Device
1110 Braid
1112 Inner Sheath
1114 Outer Sheath
1115 Sliding End
1116 Locking Tab
1120 Widest Circumference
1200 Retention Device
1210 Braid
1212 Inner Sheath
1214 Outer Sheath
1215 Sliding End
1216 Locking Tab
1220 Widest Circumference
1300 Retention Device
1314 Anchor Sleeve
1314a Chamber
1318 Anchor Mechanism
1318a Tine
1320 Port 1321 Membrane
1334 Key
1336 Key Aperture
1400 Retention Device
1410 Sheath
1412 Restraining Band
1414 Control Actuator
1416 Neck
1418 Anchor Mechanism
1418a Tine
1419 Control Member
1420 Actuator
1422 Spring
1500 Retention Device
1512 Inner Sheath
1514 Outer Sheath
1516 Neck
1518 Anchor Mechanism
1518a Tine
S Skin
V Vessel Construction As shown in FIG. 1, the present invention comprises a retention device 10 which is useful for securing catheters 12 and other medical devices beneath the skin S of a patient. As shown in FIGS. 1 and 2, the invention comprises an anchor sleeve 14 which is integrally attached to an introducer sheath 16 by such means as co-injection molding or co-extrusion. Additional methods of attachment between the anchor sleeve 14 and introducer sheath 16, including but not limited to gluing, ultrasonic welding, mechanical fasteners, heat shrinkable tubing or thermal melting are also contemplated by and therefore within the scope of the invention. As shown in FIGS. 2 and 2a, the anchor sleeve 14 defines a chamber 14a and the introducer sheath 16 defines a lumen 16a. The chamber 14a further defines a floor 14b towards the distal end (unnumbered) of the anchoring sleeve 14 which sealably houses the anchor mechanism 18, 118, 218. The interior of the chamber 14a may be lined with PTFE (not shown) to facilitate movement of the anchor mechanism 18, 118, 218 within it. A sealed chamber 14a is advantageous as it resists and minimizes the flow of blood and other bodily fluids into and out of the retention device 10 during the period of anchoring and catheterization, which could cause infection due to the potentially relatively long period of placement of the retention device 10 within the patient's body. An additional advantage to a sealed chamber 14a is that tissue in-growth is resisted, which could otherwise potentially interfere with and cause seizure of the anchor mechanism 18, 118, 218 thereby making normal removal impossible. A hemostasis valve 26, which is well known in the art, is attached to the proximal end (unnumbered) and collinear with the introducer sheath 16 to prevent the leakage of blood and other bodily fluids from the device 10 during use. The inner diameter of the lumen 16a is sized to be able to accommodate the outer diameter of a catheter 12. Thus, when the device 10 is inserted into a patient, a catheter 12 or other medical device (not shown) will extend first through the hemostasis valve 26, then through the lumen 16a and finally into the desired vessel V, organ (not shown) or body cavity (not shown).

A number of ports 20 in equal number to the number of tines 18a, 118a, 218a are formed through the anchor sleeve 14 to permit deployment of the tines 18a, 118a, 218a during treatment. In a preferred embodiment, a thin membrane 22 of a suitable plastic material such as polyurethane, silicone or latex covers the ports 20. The membrane 22 serves to seal the retention device 10 prior to deployment of the tines 18a, 118a, 218a. As explained in greater detail below, during deployment the tines 18a, 118a, 218a will puncture the membrane 22.

As best shown in FIGS. 3-5, another embodiment of the retention device 100 comprises an anchoring sleeve 114 integrally attached to a catheter 112 (and associated structures such as a hub/body) or other medical devices by such means as co-injection molding or co-extrusion. The anchoring sleeve 114 further defines a chamber 114a, which may be coated with PTFE (not shown) to facilitate movement of the anchor mechanism 18, 118, 218. In additional embodiments the anchoring sleeve 114 can be attached to the catheter 112 by any other suitable means, such as by gluing, ultrasonic welding, mechanical fasteners or thermal melting means. The chamber 114a further defines a floor 114b towards the distal end (unnumbered) of the anchor sleeve 114 and also sealably accommodates the anchor mechanism 18, 118, 218 which, as explained in detail below, extends to form lock spring 29, 129. This resists and minimizes the inflow of blood and other bodily fluids into the retention device 100 during the period of anchoring and catheterization, which could cause infection due to the potentially relatively long period of placement of the retention device 100 within the patient's body. An additional advantage to a sealed chamber is that tissue in-growth is resisted, which could otherwise potentially interfere with and cause seizure of the anchor mechanism 18, 118, 218 thereby making normal removal impossible. In a manner similar to that shown in FIG. 1 with regard to the embodiment of the retention device 10, this embodiment of the retention device 100 is likewise introduced (not shown) through a patient's skin S and into a vessel V or other anatomical site prior to deployment of the tines 18a, 118a, 218a to secure the retention device 100 to the patient's body.

A number of ports 120 in equal numbers to the numbers of tines 18a, 118a, 218a are formed through a side wall (unnumbered) of the anchor sleeve 114 to permit deployment of the tines 18a, 118a, 218a during treatment. In a preferred embodiment, a thin membrane 22 of a suitable low durometer plastic material such as polyurethane, silicone and latex covers the ports 120. The membrane 22 serves to seal the retention device 10 prior to deployment of the tines 18a, 118a, 218a. As explained in greater detail below, during deployment, the tines 18a, 118a, 218a will puncture the membrane 22.

Suitable materials for the anchor sleeve 14, 114 and introducer sheath 16 include various plastic materials including polyurethane, polyimide, PBAX, polyethylene or PTFE reinforced by stainless steel, titanium or nitinol braid 24 or coil (not shown). Carbon fiber materials comprise an alternative braiding material. Titanium, nitinol or stainless steel tubing are alternative reinforcement materials. The reinforcing braid 24 or alternative reinforcement is necessary to add additional strength to constrain the tines 18a, 118a, 218a from premature deployment through the anchor sleeve. In an alternative embodiment, as shown in FIGS. 2a and 2b, the anchor sleeve 14, 114 is reinforced by a liner 36 made of a stronger material such as ultra high density polyethylene, high density polyethylene or nylon and derivatives or combinations of the above. The liner 36 can be a separately molded inserted piece or be incorporated into the anchor sleeve 14, 114 during the molding process. It is also contemplated to insert a liner 36 impregnated (not shown) with a braid 24 or coil (not shown).

The outer surfaces (unnumbered) of the retention device 10, 100 can be coated (not shown) with a variety of commercially available compounds. These include but are not limited to antithrombogenic, antibacterial, or anti-inflammatory compounds to reduce tissue ingrowth, or prevent infection due to the presence of the retention device 10, 100 in the patient for extended periods. These compounds are also useful in improving the biocompatibility of the retention device 10, 100 and include but are not limited to heparin complex solutions, benzalkonium heparinate, triodoecylmethylammonium heparinate, chlorhexidine-silver sulfadiazine, myococycline and rifampin.

Upon introducing a catheter, sheath introducer, or other medical device incorporating the retention device 10 through a patient's skin S and into a vessel V such as an artery (not specifically shown), vein (not specifically shown) or other duct (not specifically shown), vessel or organ (not specifically shown), the tines 18*a*, 118*a*, 218*a* of the anchor mechanism 18, 118, 218 are deployed through the ports 20, 120 thereby securing the catheter 12, 112, introducer sheath 16 or other device (not shown) to the patient's body subcutaneously. The mechanism facilitating tine 18*a*, 118*a*, 218*a* deployment is more fully explained below.

Figures 6A, 7:
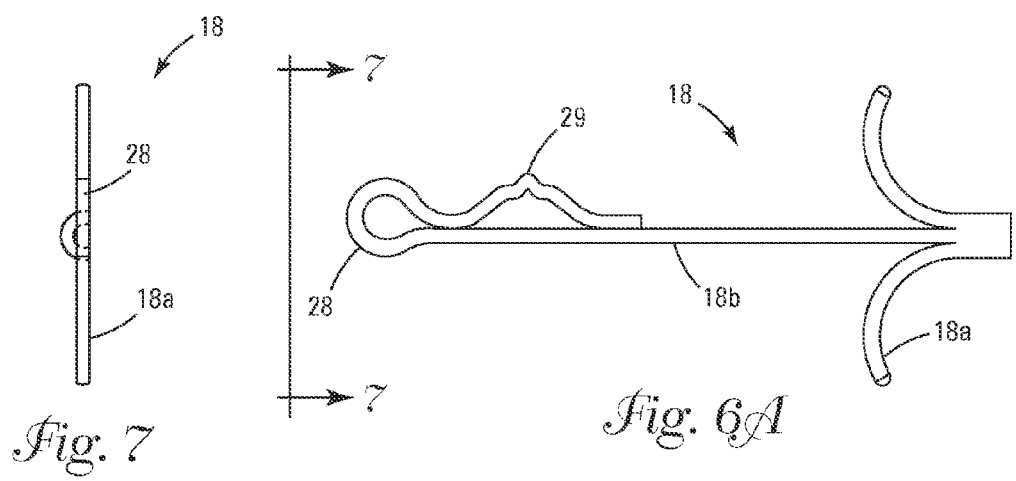
Figure 6B:
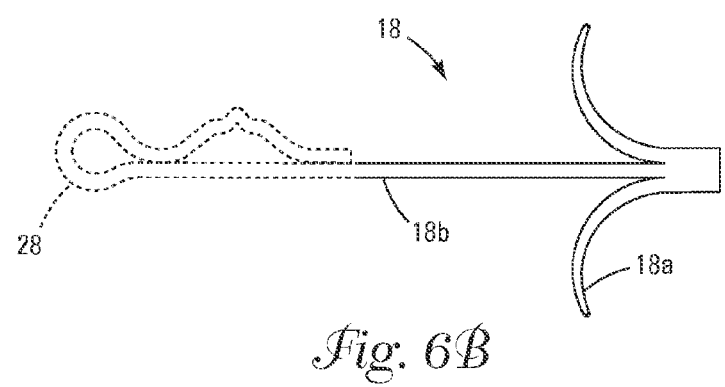
FIG. 6b is a side view of an embodiment of the anchor mechanism having tapered tines.
Figure 8:
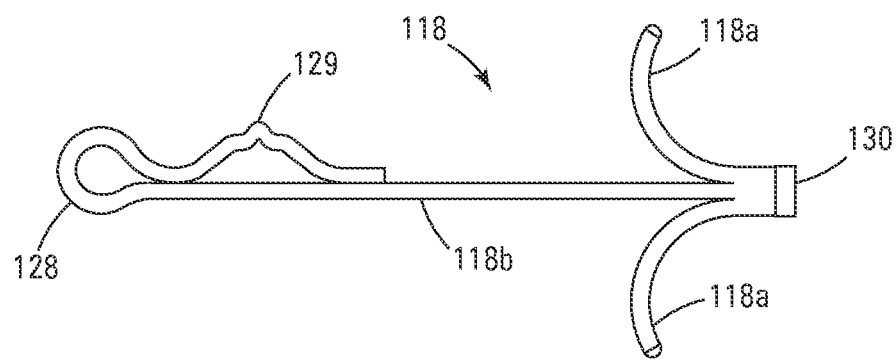
FIG. 8 is a side view of an embodiment of the anchor mechanism.
Figure 9:
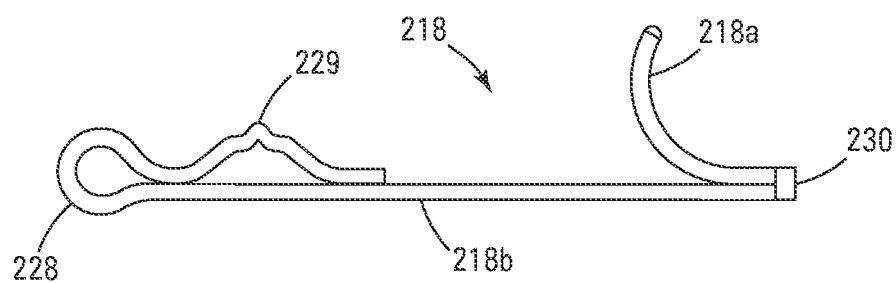
FIG. 9 is a side view of an embodiment of the anchor mechanism.
Figure 10:
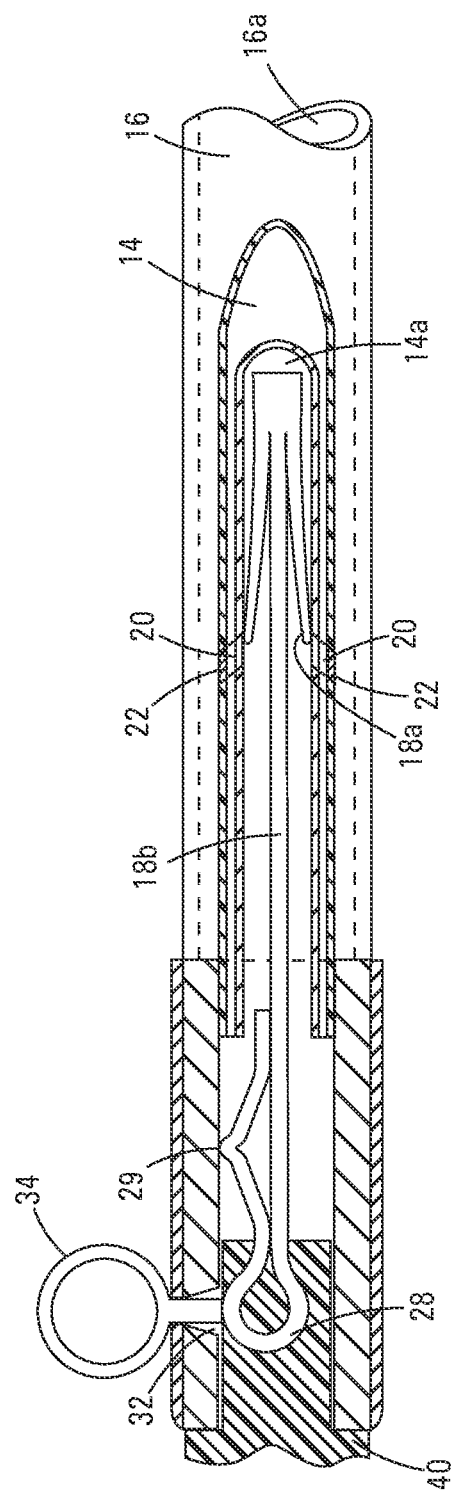
FIG. 10 is a cut away view of an embodiment of the retention device showing the lock mechanism prior to deployment of the tines and showing the key inserted into the recess.
Figure 14:
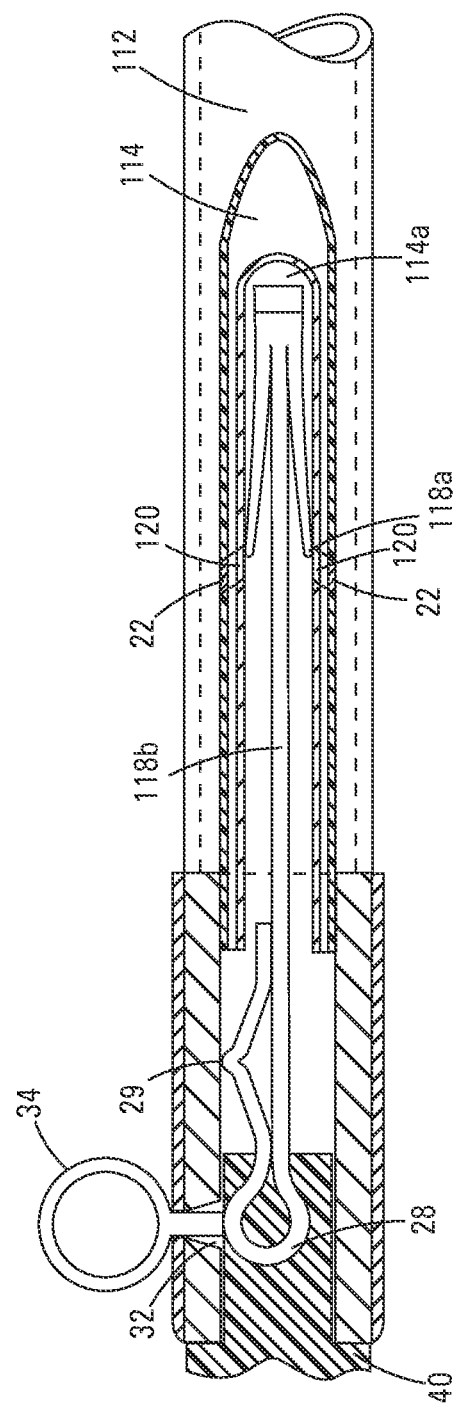
FIG. 14 is a cut away view of an embodiment of the retention device showing the lock mechanism prior to deployment of the tines.
Figure 15:
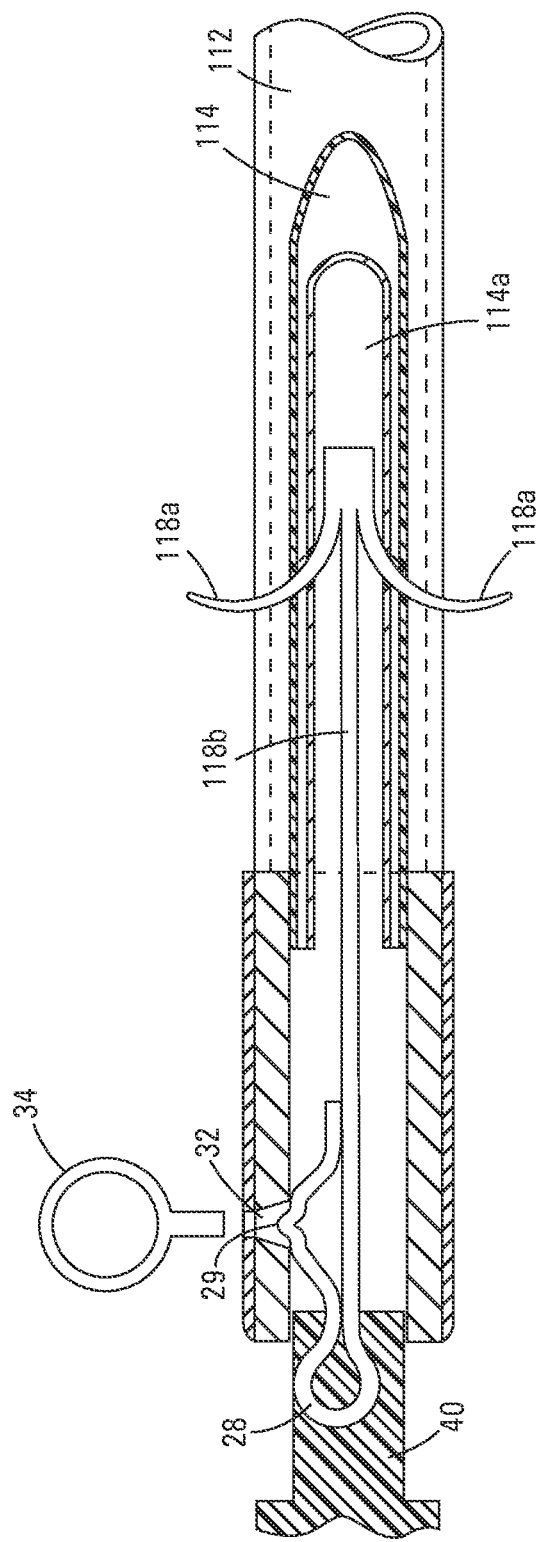
FIG. 15 is a cut away view of an embodiment of the retention device showing the lock mechanism following deployment of the tines.

An embodiment of an anchor mechanism 18 is best shown in FIGS. 6*a*, 6*b* and 7. This embodiment of the anchor mechanism 18 comprises at least a single tine 18*a* and in a preferred embodiment has two tines 18*a* but may also have additional numbers of tines 18*a* such as three (not shown), four (not shown), five (not shown), six (not shown) or even greater numbers of tines 18*a* (not shown). The tips (unnumbered) of the tines 18*a* may be sharp (not shown), dull as shown in FIG. 2*b* or rounded as shown in FIGS. 6*a* and 8-9. A control rod 18*b* is integrally attached to the tines 18*a*. At the proximal end (unnumbered) of the control rod 18*b* is an eyelet 28 formed integrally with the control rod 18*b*, which serves either as a convenient grip or as the connector for an attached handle 40. The control rod 18*b* extends proximally and is trained to bend over to form an eyelet 28. The control rod 18*b* and eyelet 28 then reverse direction to a distal direction to form the lock spring 29 which is raised above the length of the control rod 18. Together the tines 18*a* and control rod 18*b* comprise the anchor mechanism 18. As will be explained in greater detail below, deployment of the tines 18*a* through the ports 20, 120 in the anchor sleeve 14, 114 secures the retention device 10, 100 within the body of the patient for a period sufficient to complete the desired treatment. Moving the control rod 18*b* in a proximal direction thus simultaneously moves the fixedly attached tines 18*a* in a proximal direction, eventually causing the tines 18*a* to extend through the ports 20, 120 following introduction of the retention device 10, 100 within a patient. As shown in FIG. 6*a* the tines 18*a* may have a consistent width or, in an alternative embodiment, as shown in FIG. 6*b*, the tines 18*a* may be tapered.

In one embodiment, making the anchor mechanism 18 involves acquiring nitinol tubing having a length sufficient to allow a control rod 18*b* long enough to extend through the proximal end of the anchor sleeve 14, 114 so as to be able to connect control rod 18*b* to the handle 40. The tubing preferably has a wall thickness between 0.005 to 0.030 inches, however, lesser and greater wall thicknesses are also contemplated by and therefore within the scope of the invention. Portions of the length of tubing are then cut away by means of well known techniques such as EDM (electron discharge machining), laser cutting, traditional machining or water jet. The remaining portions of the tubing comprise the anchor mechanism 18, and its integrally attached tines 18*a*, control rod 18*b*. As explained in detail above, eyelet 28 and lock spring 29 are formed following cutting of the nitinol tubing. Using this manufacturing technique, anchor mechanisms 18 having wide variations are possible. It is also contemplated by the invention to make an integral anchor mechanism 18 from a flat sheet of nitinol. In this embodiment, at least the tines 18*a* and lock spring 29 are processed so as to have a trained shape when in an unrestrained state somewhere below human body temperature of 37 degrees C. The trained shape of the tines 18*a* can be a partial arc as shown in FIGS. 2*b*, 6*a*, 6*b* 7, 8, 9, 11, 13 and 15, a semi circular arc (not shown) or even a complete arc (not shown). It should be mentioned that the anchor mechanism could also be made from stainless steel or other alloys such as elgiloy, MP35N, incoloy, other superalloys or plastically deformable materials.

Two alternative embodiments of the anchor mechanism 118, 218 are shown in FIGS. 8 and 9. These anchor mechanisms 118, 218 differ from the anchor mechanism 18 shown in FIGS. 6*a*, 6*b* and 7 in that they are constructed from pieces of nitinol ribbon wire comprising tines 118*a*, 218*a* and control rod 118*b*, 218*b* having welds 130, 230 at a distal end (unnumbered) of the anchor mechanism 118, 218. In a preferred embodiment the welds 130, 230 are accomplished by a laser, however, other welding technologies such as resistance welding and friction welding could also be used. Additionally, hypotubing could used to attach the tines 118*a*, 218*a* to the control rod 118*b*, 218*b*. The anchor mechanism 118 shown in FIG. 8 has two tines 118*a* welded to the control rod 118*b*; the anchor mechanism 218 shown in FIG. 9 has only a single tine 218*a* welded to the control rod 218*b*. Control rod 118*b*, 218*b* extends proximally and is trained to bend over to form an eyelet 128, 228. The wire forming the control rod 118*b*, 218*b* and eyelet 128, 228 then reverse direction to a distal direction to form the lock spring 129, 229 which is raised above the length of the control rod 118*b*, 218*b*. Anchor mechanisms 118, 218 function in a similar manner as the anchor mechanism 18 described above. FIG. 12 shows an additional embodiment of the anchor mechanism 218 loaded into the retention device 10 prior to deployment of the tine 218*a*. FIG. 13 shows this embodiment of the anchor mechanism 218 loaded into the first embodiment of the retention device 10 following deployment of the tine 218*a*.

As shown in FIGS. 10-11 and 14-15, the retention device 10, 100 is provided with a lock mechanism (unnumbered) comprising a lock spring 29 and a recess 32. In the undeployed configuration, the lock spring 29 is compressed against the inner dimension (unnumbered) of the chamber 14*a*, 114*a*. This is due to the normal, trained shape of the lock spring 29 being greater than the inner dimension (unnumbered) of the chamber 14*a*, 114*a*. When the control rod 18*b*, 118*b* is distally moved by the physician, as discussed above, the tines 18*a*, 118*a*, 218*a* will deploy through the ports 20, 120. Upon reaching a predetermined proximal distance, when the tines 18*a*, 118*a*, 218*a* are fully deployed, the lock spring 29 will reach the internal recess 32 of the chamber 29 and move outward, to fit into the recess 32, thus locking the retention device 10, 100 in the deployed position and securing it in place in the patient. To remove the retention device 10, 100 a key 34 is provided which permits the physician to externally depress the lock spring 29, thus making distal movement of the control rod 18*b*, 118*b* possible, allowing eventual removal of the retention device 10, 100 from the patient. It is also contemplated and therefore within the scope of the invention to have a series of recesses (not shown) along the length of the inner dimension of the chamber 14*a*, 114*a* allowing the physician a degree of control over the amount of tine 18*a*, 118*a*, 218*a* that is deployed.

Figure 16:
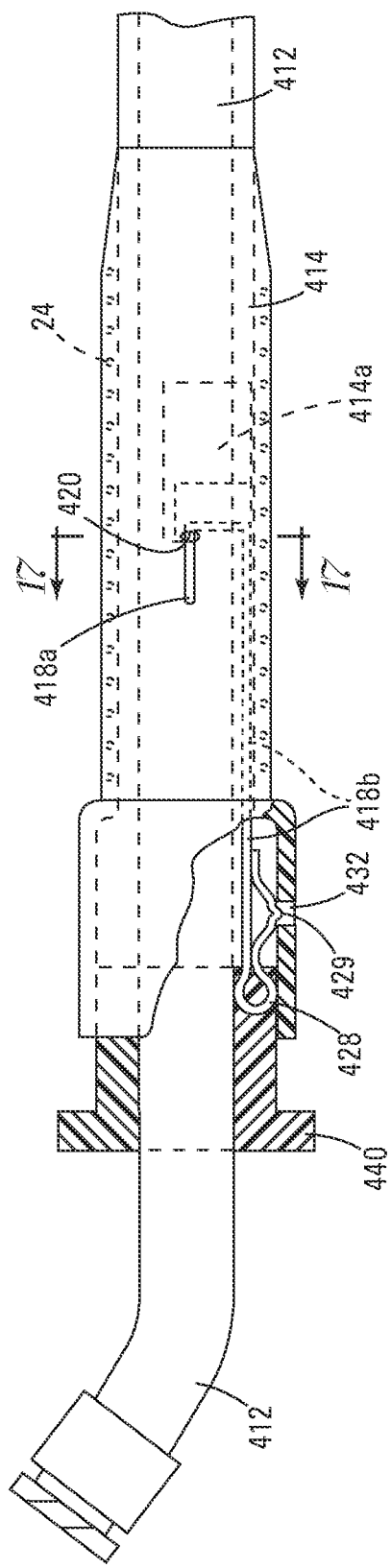
FIG. 16 is a side view of an embodiment of the retention device showing the anchor mechanism in phantom and the locking mechanism in a cut away view.
Figure 17:
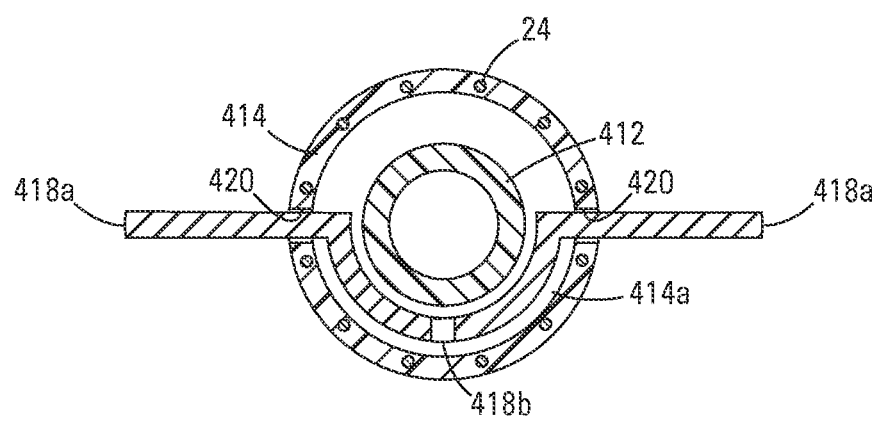
FIG. 17 is a cross sectional view taken through the lines 17-17 of the embodiment of the retention device shown in FIG. 16.

FIG. 16 shows an additional embodiment of the retention device 400 where the anchor mechanism 418 surrounds the lumen 412 of the catheter 412 to which an anchor sleeve 414 is attached. The anchor sleeve 414 defines a chamber 414*a* into which the anchor mechanism 418 is loaded prior to deployment. A control rod 418*b* is distally attached to a plurality of tines 418*a*. When the control rod 418*b* is moved proximally the tines 418*a* will extend through ports 420 that correspond to the individual tines 418*a* as more fully discussed above. The retention device 400 is fitted with a lock spring 429 which fits into a recess 432 following deployment of the tines 418*a*. An eyelet 428 is formed at the proximal end (unnumbered) of the control rod 418*b*. A handle 440 is preferably attached around the eyelet 428 to facilitate deployment of the tines 418*a* following insertion into the patient. FIG. 17 shows a cross sectional view of the embodiment of the retention device 400 following deployment of the tines 418*a*.

Figure 18A:
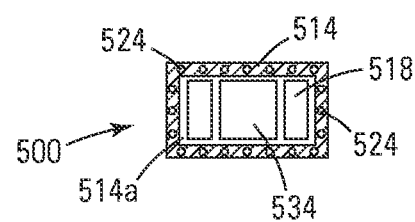
Figure 19A:
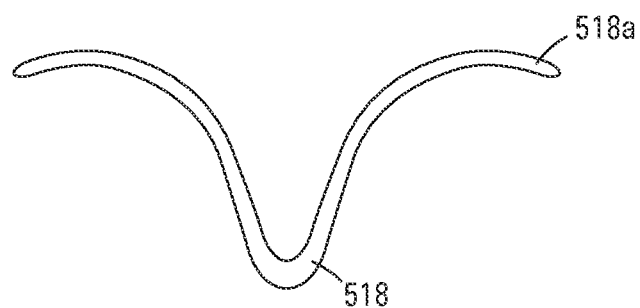
FIG. 19a shows the anchor mechanism of the embodiment shown in FIG. 19 removed from the retention device.

FIG. 18 shows an embodiment of the retention device 500 in the undeployed configuration, with the tine(s) 518*a* retracted inside the chamber 514*a*. FIG. 19 shows the anchoring device 500 in the deployed configuration, following deployment of the tine(s) 518*a* through the port(s) 520. In this embodiment 500, the anchor mechanism 518 is loaded into an anchor sleeve 514, defining a chamber 514*a* which serves to house the anchor mechanism 518 and spring 522. It should be mentioned that additional biasing means are contemplated by and therefore within the scope of the invention. Additional biasing means include hydraulic and pneumatic cylinders (not shown) and various kinds of plastic materials (not shown) having spring-like characteristics. A number of ports 520 in equal number to the number of tines 518*a* are formed through the anchor sleeve 514 to permit deployment of the tines 518*a* during deployment during treatment. In a preferred embodiment, a thin membrane 521 of a suitable plastic material such as polyurethane, silicone or latex covers the port(s) 520. The membrane 521 serves to seal the retention device 500 prior to deployment of the tine(s) 518*a*. A sealed chamber 514*a* is advantageous as it resists and minimizes the flow of blood and other bodily fluids into and out of the retention device 500 during the treatment period which could cause infection due to the potentially long period of placement of the retention device 500 within the patient's body. An additional advantage to a sealed chamber 514*a* is that tissue in-growth is resisted, which could otherwise potentially interfere with or cause seizure of the anchor mechanism 518 thereby making normal removal difficult if not impossible. The anchor mechanism 518 is formed in a generally "U" shaped configuration and has at least a single tine 518*a* which is terminated by a free end (unnumbered) and an inner end 518*b*, which is opposite the free end (unnumbered). In the embodiment of the anchoring device 500 as shown in FIGS. 18-19*a*, the anchor mechanism 518 is a unitary, integrated element, however, it is also contemplated to have the anchor mechanism 518 be made of attached, separately manufactured pieces (not shown). An unattached spring 522 is placed into the chamber 514*a* proximate the inner end 518*b* to provide a bias to the anchor mechanism 518 such that it will default in a manner where the tine(s) 518*a* extend or deploy from the anchor sleeve 514 through the port(s) 520. The anchor mechanism 518 is preferably made from nitinol which has been processed to exhibit superelasticity at a temperature below human body temperature. The nature, processing and advantages of superelasticity are discussed in detail below. Additional materials for building the anchor mechanism 518 include but are not limited to stainless steel, elgiloy, MP35N, incoloy, other superalloys or plastically deformable materials.

Figure 18B:
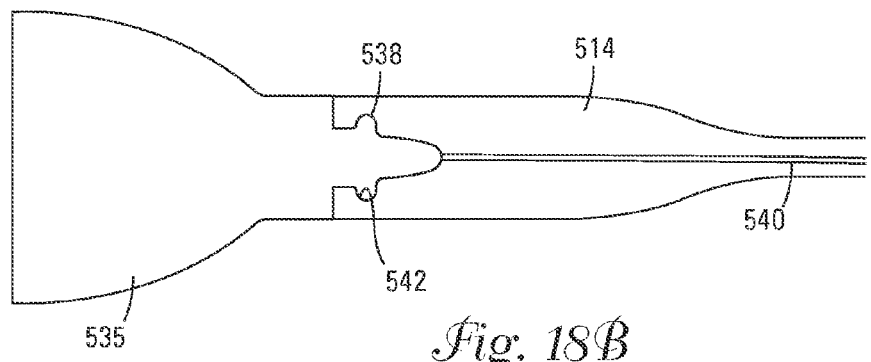
FIG. 18b is a cut away side view of the key and a portion of the anchor sleeve, in the undeployed configuration, with the key inserted.
Figure 19B:
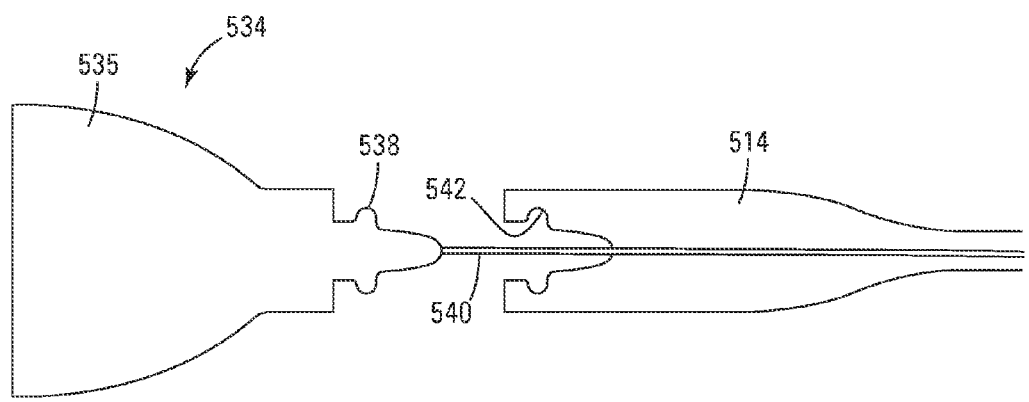
FIG. 19b is a cut away side view of the key and a portion of the anchor sleeve, in the deployed configuration, with the key removed.

A key 534 is provided which is shaped and sized to fit into the key aperture 536 whereby when the key 534 is inserted into the key aperture 536 the tine(s) 518*a* is/are replaced inside the anchor sleeve 514. FIG. 18*b* shows in greater detail the key 534 inserted into the anchor sleeve 514. The key itself comprises a handle 535 which is attached to a locking stop 538 which extends from the handle 535. Extending from the locking stop 538 is a shaft 540 having a diameter (unnumbered) sized to fit within the key aperture 536 and a length (unnumbered) sufficient to contact the anchor mechanism 518. The anchor sleeve 514 further defines a locking recess 542 which is dimensioned to have a concave interior profile that snugly mates with the outer contours (unnumbered) of the locking stop 538 on the key 534, providing a snap lock fit that maintains the key 534 and retaining device 500 in the undeployed configuration as shown in FIG. 18*b* as long as it is inserted. Either or both the anchor sleeve 514 or the locking stop 538 are made from polyurethane, polyimide, PBAX, polyethylene or PTFE which, because of their partially elastic nature, allows the locking stop 538 and locking recess to be used as a snap lock. FIG. 19*b* shows the key 534 removed from the anchor sleeve 514 following deployment of the anchor mechanism 518. FIGS. 18*b* and 19*b* are specifically directed to the details of the key 534 and associated structures as applying to the embodiment of the retention device 500 shown in FIGS. 18-19*b*. It should further be mentioned that the other embodiments of the retention device 600, 700, 800, 1300 utilizing an anchor sleeve 614, 714, 814, 1314 described herein, while not showing the details shown in FIGS. 18*b* and 19*b*, have similar locking key structures (not shown) incorporated that allow the physician to control deployment of the anchor mechanism 618, 718, 818, 1318.

Suitable materials for the anchor sleeve 514 include various plastic materials including polyurethane, polyimide, PBAX, polyethylene or PTFE reinforced by stainless steel, titanium or nitinol braid 524 or coil (not shown). Carbon fiber materials comprise an alternative braiding material. The reinforcing braid 524 is desirable to add additional wall strength to constrain the tines 518*a* from uncontrolled deployment through the anchor sleeve 514. In an alternative embodiment, as shown in FIG. 20*b*, the anchor sleeve 614 is reinforced by a liner 638 made of a stronger material such as ultra high density polyethylene, high density polyethylene or nylon and derivatives or combinations of the above. The liner 638 can be a separately molded inserted piece or be incorporated into the anchor sleeve 614 during the molding process. It is also contemplated to insert a liner (not shown) impregnated (not shown) with a braid (not shown) or coil (not shown). While the liner 638 is shown illustrating the embodiment of the retention device 600 as shown in FIGS. 20-20*b*, the concept of a liner 638 is equally applicable to the other embodiments 500, 600, 700, 800, 1300 discussed herein.

The outer surfaces (unnumbered) of the retention device 500 can be coated (not shown) with a variety of commercially available compounds. These include but are not limited to antithrombogenic, antibacterial, or anti-inflammatory compounds to reduce tissue ingrowth, or prevent infection due to the presence of the retention device 500 in the patient for extended periods. These compounds are also useful in improving the biocompatibility of the retention device 500 and include but are not limited to heparin complex solutions, benzalkonium heparinate, triiodoecylmethylammonium heparinate, chlorhexidine-silver sulfadiazine, myococycline and rifampin.

Figure 20A:
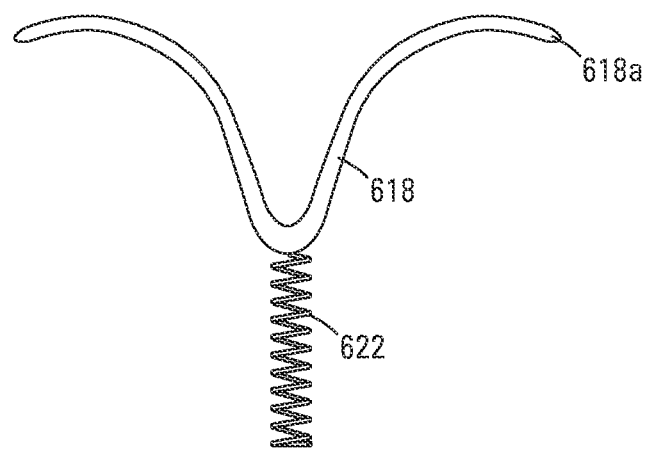
FIG. 20a is a side view of the anchor mechanism with attached spring used in the embodiment shown in FIG. 20, removed from the retention device.
Figure 20B:
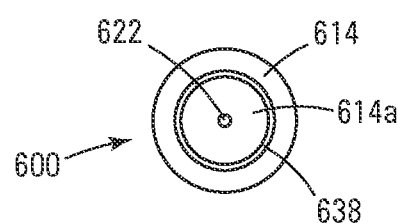
FIG. 20b is a cross section of the embodiment of the retention device shown in FIG. 20 taken along the line 20b-20b.

Yet another embodiment of the retention device 600 is shown in FIGS. 20-20b. This embodiment 600 is similar to the embodiment of the retention device 500 shown in FIGS. 18 and 19 and differs mainly in having the spring 622 attached proximate the inner end 618b of the anchor mechanism 618 by welding, gluing, crimping, fasteners or any other secure and permanent method. The retention device 600 shown in FIG. 20 has an anchor sleeve 614 defining a chamber 614a, which serves to house the anchor mechanism 618 and spring 622. The anchor mechanism 618 is formed in a generally "U" shaped configuration and has at least a single tine 618a which terminates in a free end (unnumbered) and an inner end 618b, which is opposite the free end (unnumbered). In the embodiment of the anchoring device 600 as shown, the anchor mechanism 618 is a unitary, integrated element, however, it is also contemplated to have the anchor mechanism 618 be made of attached, separately manufactured pieces (not shown). A key 634 is provided which is shaped and sized to fit into a key aperture 636 whereby when the key 634 is pushed into the key aperture 636 the tine(s) 618a is/are replaced inside the chamber 614a.

Suitable materials for the anchor sleeve 614 include various plastic materials including polyurethane, polyimide, PBAX, polyethylene or PTFE reinforced by stainless steel, titanium or nitinol braid (not shown) or coil (not shown). Carbon fiber materials comprise an alternative braiding material. The reinforcing braid (not shown) is desirable to add additional strength to constrain the tines 618a from premature deployment through the anchor sleeve 614. In an alternative embodiment, as shown in FIG. 20b, the anchor sleeve 614 is reinforced by a liner 638 made of a stronger material such as ultra high density polyethylene, high density polyethylene or nylon and derivatives or combinations of the above. The liner 638 can be a separately molded inserted piece or be incorporated into the anchor sleeve 614 during the molding process. It is also contemplated to insert a liner 638 impregnated (not shown) with a braid or coil (not shown).

The outer surfaces (unnumbered) of the retention device 600 can be coated (not shown) with a variety of commercially available compounds. These include but are not limited to antithrombogenic, antibacterial, or anti-inflammatory compounds to reduce tissue ingrowth, or prevent infection due to the presence of the retention device 600 in the patient for extended periods. These compounds are also useful in improving the biocompatibility of the retention device 600 and include but are not limited to heparin complex solutions, benzalkonium heparinate, triodoecylmethylammonium heparinate, chlorhexidine-silver sulfadiazine, myococycline and rifampin.

Figure 21A:
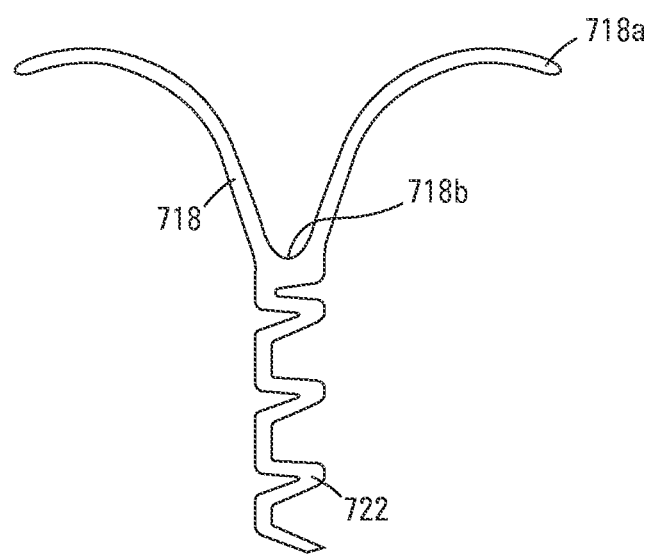
FIG. 21a is a side view of the anchor mechanism of the embodiment shown in FIG. 21 removed from the retention device.

Still another embodiment of the retention device 700 is shown in FIG. 21. This embodiment 700 is similar to the embodiments shown in FIGS. 18-20b and differs mainly in having the spring 722 integrally attached proximate the inner end 718b. The anchoring device 700 shown in FIG. 21 has an anchor sleeve 714 defining a chamber 714a, which serves to house the anchor mechanism 718 and integrally attached spring 722. A number of ports 720 in equal number to the number of tines 718a are formed through the anchor sleeve 714 to permit deployment of the tines 718a during deployment during treatment. In a preferred embodiment, a thin membrane 721 of a suitable plastic material such as polyurethane, silicone or latex covers the port(s) 720. The membrane 721 serves to seal the retention device 700 prior to deployment of the tine(s) 718a. A sealed chamber 714a is advantageous as it resists and minimizes the flow of blood and other bodily fluids into and out of the retention device 700 during the treatment period which could cause infection due to the potentially long period of placement of the retention device 700 within the patient's body. An additional advantage to a sealed chamber 714a is that tissue in-growth is resisted, which could otherwise potentially interfere with or cause seizure of the anchor mechanism 718 thereby making normal removal difficult if not impossible. The anchor mechanism 718 is formed in a generally "U" shaped configuration and has at least a single tine 718a which is terminated by a free end and an inner end 718b, which is opposite the free end. In the embodiment of the anchoring device 700 as shown, the anchor mechanism 718 is a unitary, integrated element, however, it is also contemplated to have the anchor mechanism 718 be made of attached, separately manufactured pieces (not shown). An unattached spring 722 is placed into the anchor sleeve 714 proximate the inner end 718b to provide a bias to the anchor mechanism 718 such that it will default in a manner where the tine(s) 718a extend or deploy from the anchor sleeve 714 through the port(s) 720. A key 734 is provided which is shaped and sized to fit into a key aperture 736 whereby when the key 734 is pushed into the key aperture 736 the tine(s) 718a is/are replaced inside the anchor sleeve 714.

Suitable materials for the anchor sleeve 714 include various plastic materials including polyurethane, polyimide, PBAX, polyethylene or PTFE reinforced by stainless steel, titanium or nitinol braid or coil (not shown). Carbon fiber materials comprise an alternative braiding material. The reinforcing braid (not shown) is desirable to add additional wall strength to constrain the tines 718a from premature deployment through the anchor sleeve 714. In an alternative embodiment (not shown) the anchor sleeve 714 is reinforced by a liner (not shown) made of a stronger material such as ultra high density polyethylene, high density polyethylene or nylon and derivatives or combinations of the above. The liner (not shown) can be a separately molded inserted piece or be incorporated into the anchor sleeve 714 during the molding process. It is also contemplated to insert a liner (not shown) impregnated (not shown) with a braid or coil (not shown).

The outer surfaces (unnumbered) of the retention device 700 can be coated (not shown) with a variety of commercially available compounds. These include but are not limited to antithrombogenic, antibacterial, or anti-inflammatory compounds to reduce tissue ingrowth, or prevent infection due to the presence of the retention device 700 in the patient for extended periods. These compounds are also useful in improving the biocompatibility of the retention device 700 and include but are not limited to heparin complex solutions, benzalkonium heparinate, triodoecylmethylammonium heparinate, chlorhexidine-silver sulfadiazine, myococycline and rifampin.

Figure 22A:
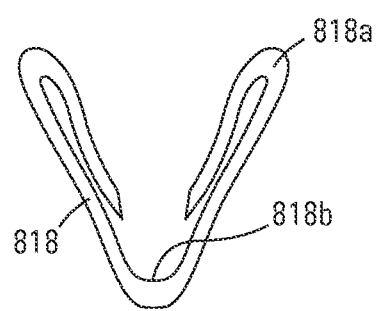
FIG. 22a is a side view of the anchor mechanism of the embodiment shown in FIG. 22 removed from the retention device.

FIG. 22 shows an alternative embodiment of the retention device 800 in the deployed configuration. FIG. 23 shows the retention device 800 shown in FIG. 22 in the undeployed configuration. The embodiment of the retention device 800 is similar to the embodiments 500, 600, 700 shown in FIGS. 18-21a with the difference being that the anchor mechanism 518, 618, 718 having tines 518a, 618a, 718a is replaced by atraumatic loops 818a. The loops 818a are, in essence, longer tines that have been processed to bend back around themselves to form a tight "U", the free end (unnumbered) of which remains inside the chamber 814a at all times. The advantage of this configuration is that rounded loop(s) 818*a* are less likely to puncture or lacerate contacted tissue during the treatment period when the patient's physical movement might cause a slight disruption of the retention device 800 and coupled medical device. The anchor mechanism 818 is loaded into an anchor sleeve 814 defining a chamber 814*a* which serves to house the anchor mechanism 818 and spring 822 and is further provided with a number of ports 820 equal to the number of loops 818*a* which are attached to the anchor mechanism 818. The ports 820 are formed through the anchor sleeve 814 to permit deployment of the loops 818*a* during deployment during treatment. In a preferred embodiment, a thin membrane 821 of a suitable plastic material such as polyurethane, silicone or latex covers the port(s) 820. The membrane 821 serves to seal the retention device 800 prior to the deployment of the loop(s) 818*a*. A sealed chamber 814*a* is advantageous as it resists and minimizes the flow of blood and other bodily fluids into and out of the retention device 800 during the treatment period which could cause infection due to the potentially long period of placement of the retention device 800 within the patient's body. An additional advantage to a sealed chamber 814*a* is that tissue in-growth is resisted, which could otherwise potentially interfere with or cause seizure of the anchor mechanism 818 thereby making normal removal difficult if not impossible.

In the embodiment of the anchoring device 800 as shown in FIGS. 22-23, the anchor mechanism 818 is a unitary, integrated element, however, it is also contemplated to have the anchor mechanism 818 be made of attached, separately manufactured pieces (not shown). An spring 822 is placed into the anchor sleeve 814 proximate the inner end 818*b* to provide a bias to the anchor mechanism 818 such that it will default in a manner where the loop(s) 818*a* extend or deploy from the anchor sleeve 814 through the port(s) 820. The anchor mechanism 818 is preferably made from nitinol which has been processed to exhibit superelasticity at a temperature below human body temperature. The nature, processing and advantages of superelasticity are discussed in detail below. Additional materials for building the anchor mechanism 818 include but are not limited to stainless steel, elgiloy, MP35N, incoloy or other superalloys. A key 834 is provided which is shaped and sized to fit into a key aperture 836 whereby when the key 834 is pushed into the anchor sleeve 814 the tine(s) 818*a* is/are replaced inside the anchor sleeve 814.

Suitable materials for the anchor sleeve 814 include various plastic materials including polyurethane, polyimide, PBAX, polyethylene or PTFE reinforced by stainless steel, titanium or nitinol braid (not shown) or coil (not shown). Carbon fiber materials comprise an alternative braiding material. The reinforcing braid (not shown) is desirable to add additional strength to constrain the loop(s) 818*a* from premature deployment through the anchor sleeve 814. In an alternative embodiment, as shown in FIG. 18*b*, the anchor sleeve 814 is reinforced by a liner (not shown) made of a stronger material such as ultra high density polyethylene, high density polyethylene or nylon and derivatives or combinations of the above. The liner (not shown) can be a separately molded inserted piece or be incorporated into the anchor sleeve 814 during the molding process. It is also contemplated to insert a liner (not shown) impregnated (not shown) with a braid (not shown) or coil (not shown).

The outer surfaces (unnumbered) of the retention device 800 can be coated (not shown) with a variety of commercially available compounds. These include but are not limited to antithrombogenic, antibacterial, or anti-inflammatory compounds to reduce tissue ingrowth, or prevent infection due to the presence of the retention device 800 in the patient for extended periods. These compounds are also useful in improving the biocompatibility of the retention device 800 and include but are not limited to heparin complex solutions, benzalkonium heparinate, triodoecylmethylammonium heparinate, chlorhexidine-silver sulfadiazine, myococycline and rifampin.

Figure 25A:
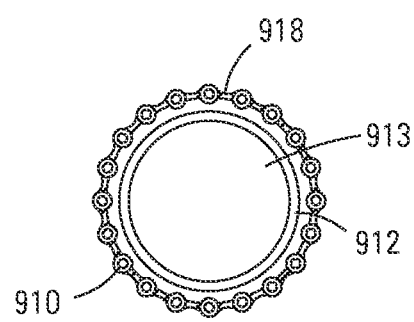
FIG. 25a is a cross section taken along the line between points 25A-25A of FIG. 25.

FIGS. 24 and 25 show another embodiment of the retention device 900 having a length of braid 910 attached at one end to an inner sheath 912 and at the other end to an outer sheath 914. As best shown in FIG. 25*a*, the inner sheath 912 defines a lumen 913 which allows fluid communication to occur between both ends of the inner sheath 912. In one embodiment, the inner sheath 912 may actually be a catheter (not shown) or other medical device used to provide communication between the inside of a patient's body and the outside. In other embodiments, the inner sheath 912 is a separate structure coupled to a catheter or other medical device. The outer sheath 914 defines an inner dimension (unnumbered) and the inner sheath 912 defines an outer dimension (unnumbered) and is sized to allow the outer sheath 914 to slidably engage the outer diameter of the inner sheath 912. In one embodiment as shown in FIGS. 24 and 25, the braid 910 is attached at one end to the inner sheath 912 which is fixed and at the other end to a sliding end 915 of the outer sheath 914, which slidably engages the inner sheath 912 and causes the braid 910 to deploy as discussed below. In another embodiment (not shown), the outer sheath 914 is fixed in position and the inner sheath 912 slidably moves to cause the braid 910 to deploy.

The nature of the attached braid 910 is such that it defines a longitudinal dimension (unnumbered) and a diameter (unnumbered) which are in inverse relationship with each other, i.e., as the longitudinal dimension (unnumbered) increases, the diameter (unnumbered) simultaneously decreases. Depending on the degree of decreasing the longitudinal dimension (unnumbered), a great variety of combinations of longitudinal dimensions and diameters is possible. The braid 910 is preferably woven from a plurality of strands (unnumbered) of nitinol alloy that is processed to exhibit superelasticity at somewhere below human body temperature. In an alternative embodiment, the braid 910 could also be made from various stainless steel alloys, polymeric materials or composite materials. It should be mentioned that the nitinol braid 910 could be processed (i.e., mechanically and heat treated) to be in either the shortened configuration as shown in FIG. 24 in an unrestrained state at somewhere below human body temperature or in the elongated configuration as shown in FIG. 25 at somewhere below human body temperature.

In a preferred embodiment, as shown FIG. 25*a*, the braid 910 is coated with an elastomeric coating 918 such as a medical grade silicone or urethane. The coating 918 completely encases the braid 910 closing the spaces (unnumbered) between individual strands (unnumbered)(i.e., forms a web) and is able to expand and/or contract as deployment occurs due to its elastomeric nature. Coating 918 is desirable because it prevents ingrowth from occurring into the braid 910 during the treatment period, which may be relatively lengthy. The invention also contemplates coating the braid 910 in a manner wherein the individual strands (unnumbered) are coated, but the spaces between the strands are open (not shown).

To deploy the retention device 900 following introduction into a patient, the braid 910 is moved from the elongated configuration as shown in FIG. 25 into the shortened configuration as shown in FIG. 24 by sliding the outer sheath 914 toward the point of braid 910 attachment on the inner sheath 912. This causes the braid 910 to shorten and widen, eventually defining a widest circumference 920 thus subcutaneously retaining the coupled medical device (not shown) within the patient for the duration of treatment. A locking tab 916 is formed into the outer sheath 914 to maintain the retention device 900 in the deployed configuration for the duration of the treatment period.

Figure 29A:
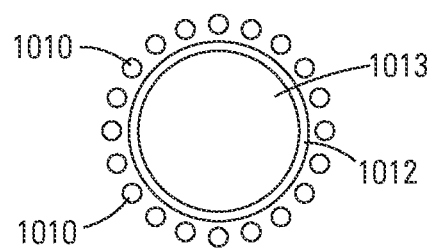
FIG. 29a is a cross section taken along the line between points B-B of FIG. 28 showing the uncoated braid.

As shown in FIGS. 28, 29 and 29a, the invention also contemplates an additional embodiment of the retention device 1000 having the braid 1010 in an uncoated version. In other aspects, this embodiment of the invention is similar to the embodiment shown in FIGS. 24, 25 and 25a.

In the embodiments of the retention device 900, 1000 it can be seen that the braid 910, 1010 when in the shortened configuration as shown in FIGS. 24 and 28 is in a symmetrical configuration. In this configuration, both sides (unnumbered) of the shortened braid 910, 1010 are approximately equal in shape and size and the widest circumference 920, 1020 extends around the longitudinal axis (unnumbered) of the inner sheath 912, 1012 at an approximate 90 degree angle. As shown in FIGS. 26 and 27, in alternative embodiments 1100, 1200 the braid 1110, 1210 can also be trained to be in an asymmetrical configuration when in the shortened state. FIG. 26 shows a braid 1110 which assumes a configuration where the widest circumference 1120 extends around the longitudinal axis (unnumbered) of the inner sheath 1112 at an approximate 45 degree/45 degree angle. FIG. 27 shows a braid 1210 which assumes a configuration where the widest circumference 1220 extends around the longitudinal axis (unnumbered) of the inner sheath 1212 at an approximate 60 degree/30 degree angle. The advantage of the asymmetric braid configurations shown in FIGS. 26-27 is that the medical device (unnumbered) attached to the retention device 1100, 1200 extends from the patient at a more comfortable and stable angle. It is also possible to achieve asymmetric shortened braid configurations by means of asymmetrical braiding techniques.

Except for the asymmetrical configuration of the widest circumference 1120, 1220 the embodiments of the retention device 1100, 1200 are similar in other aspects to the embodiments of the retention device 900, 1000 discussed above.

Figure 30A:
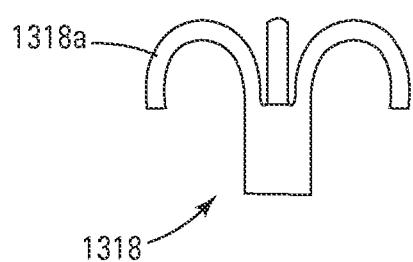
FIG. 30a is a side view of the anchor mechanism of the embodiment shown in FIG. 30, removed from the invention.
Figure 30B:
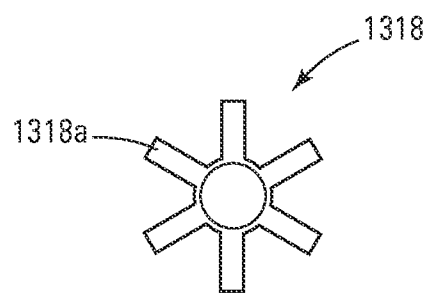
FIG. 30b is a top end view of the anchor mechanism of the embodiment shown in FIG. 30, removed from the invention.

FIGS. 30-31 show a cut away side view of a further embodiment of the invention 1300. The embodiment 1300 is similar to the embodiments 500, 600, 700, 800 shown in, respectively, FIGS. 18-23, with the difference being an anchor mechanism 1318 that is cut or machined from a length of metallic tubing. The metallic tubing can be cut by such well known methods as wire electrical discharge machining (EDM), mechanical cutting, laser cutting, water jet or traditional machining. At least one and preferably a plurality of tines 1318a is formed by cutting or removing metal along an axis parallel with the longitudinal axis of the tubing. In a preferred embodiment, the anchor mechanism 1318 is cut from a length of nitinol tubing and then at least the tine(s) 1318a are processed as described below to program the nitinol to exhibit superelasticity at somewhere below human body temperature.

Figure 32A:
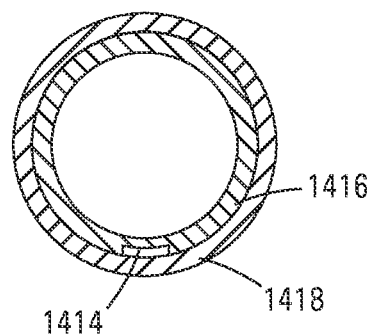
Figure 32B:
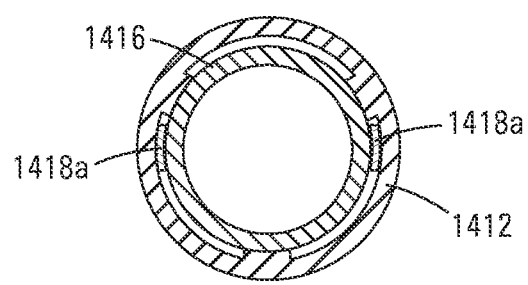
FIG. 32b shows a cross section of the embodiment shown in FIG. 32 taken through the lines 32b-32b.

FIGS. 32-33 show a cut away side view of another embodiment of the invention 1400. The retention device 1400 comprises a sheath 1410 which defines a length (unnumbered), a neck 1416 which is a section of the sheath 1410 having a lesser diameter and a groove 1414 which accommodates an actuator 1420. A retaining band 1412 surrounds the neck 1416 and is fixedly attached to the neck 1416 at several points (unnumbered). An anchor mechanism 1418 is cut or machined as described within and defines at least a single tine 1418a. The anchor mechanism 1418 as shown in FIGS. 32-33 at least partially surrounds and is externally slidably mounted to the neck 1416. The anchor mechanism is preferably made from a piece of nitinol tubing which has had sections cut away to produce free ended tines 1418a which can be trained or processed into possessing a superelastic, unrestrained, assumable shape, as discussed elsewhere. A spring 1422 is mounted to the sheath 1410 or neck 1416 and biases the anchor mechanism 1418 toward the deployed configuration as best shown in FIG. 33. An actuator 1420 is fitted into the groove 1414 and maintains the retention device 1400 in the undeployed configuration as best shown in FIG. 32 by preventing the anchor mechanism 1418 from sliding in the biased direction until the device is introduced into the patient. The actuator 1420 is connected to the anchor mechanism 1418 by a control member 1419. While in the undeployed configuration the tine(s) 1418a are held against the neck 1416 by the retaining band 1412. Because the retaining band 1412 is attached to the neck 1416 at several points, additional spaces (unnumbered) are defined through which the tine(s) 1418a can escape as the anchor mechanism 1418 slides in its biased direction, to assume the deployed configuration.

Figure 34:
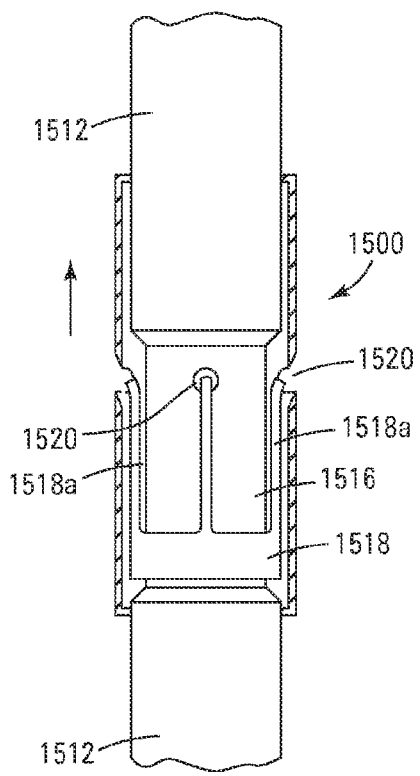
FIG. 34 is a cut away side view of an embodiment of the retention device having a fixed, externally mounted anchor mechanism in the undeployed configuration.
Figure 35:
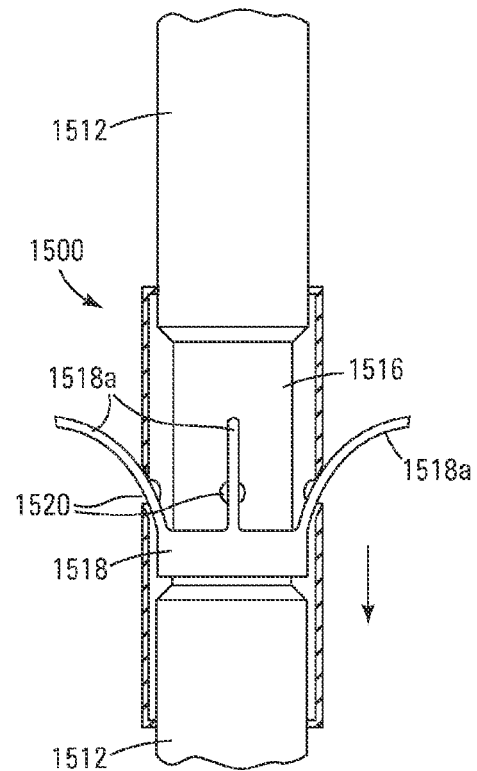
FIG. 35 is a cut away side view of the embodiment shown in FIG. 34 in the deployed configuration.

FIGS. 34-35 show a cut away side view of an embodiment of the retention device 1500. The retention device comprises an inner sheath 1512 defining a length (unnumbered), a width (unnumbered) and a neck 1516, which is a section of the inner sheath 1512 having a lesser diameter. An anchor mechanism 1518 defining at least a single tine 1518a at least partially surrounds and is externally and fixedly attached to the neck 1516. An outer sheath 1514 defines a length (unnumbered), a width (unnumbered) and a number of ports 1520 corresponding with the number of tines 1518a and is sized to slidably fit over the inner sheath 1512. To maintain the retention device 1500 in the undeployed configuration, the outer sheath 1514 is slid into a position along the length of the inner sheath 1512 to restrain the tine(s) 1518a with the tip (unnumbered) proximate the corresponding port 1520. Following successful introduction into the patient of the retention device 1500 and coupled medical device, the outer sheath 1514 is slid in a direction as shown in FIG. 35 allowing the tine(s) 1518a to escape through the ports 1520 to assume their trained shape, thus subcutaneously deploying the retention device 1500 for the duration of treatment. At the completion of treatment, the outer sheath 1514 is slid into the position shown in FIG. 34, again restraining the tine(s) 1518a allowing removal of the retention device 1500 and coupled medical device from the patient.

FIG. 36 shows a side view of the embodiment of the retention device 500 coupled with an introducer sheath 16 following successful introduction into a patient and subcutaneous deployment of the tines 518a. It is emphasized that this combination of coupled retention device 500 and medical device is exemplary and in no way intended to be limiting. Thus, the other embodiments of the retention device 10, 100, 200, 400, 600, 700, 800, 900, 1000, 1100, 1200, 1300, 1400, 1500 discussed herein could also be equally successfully coupled to a variety of other medical devices used for temporary but relatively long term placement.

All embodiments of the sutureless retention device 10, 100, 200, 400, 500, 600, 700, 800, 900, 1000, 1100, 1200, 1300, 1400, 1500 can be configured to be separately attachable to any kind of medical device. Attachment means include but are not limited to injection molding, co-extrusion, press fit, adhesives, hook and loop fastener material, snaps, retaining rings, thermal melting techniques, sonic welding, crimping, heat shrink, mechanical fasteners, or an introducer sheath.

Making the embodiments of the anchor mechanism 18, 118, 218, 518, 618, 718, 818 involves acquiring lengths of nitinol ribbon wire or sheet. In the embodiments shown in FIGS. 1-2, 6a, 6b, 7, 10, 10a, 11, 15, 18-23 the anchor mechanism 18, 518, 618, 718, 818 is made from a single piece of nitinol ribbon wire or sheet. In the embodiments shown in FIGS. 8, 9, 12, 13 and 14, separate pieces eventually becoming control rod 118b and tines 118a are then cut to appropriate lengths and attached at a distal end 130, 230 by means of laser welding. In an alternative embodiment, the tines 118a, 218a could also be attached to the control rod 118b, 218b by soldering, gluing or mechanical bonding. It should also be mentioned that anchor mechanisms 118, 218 could also be similarly made from round wire (not shown) and square wire (not shown). In the embodiment shown in FIGS. 16-17 and 30-31, the anchor mechanism 418, 1318, 1418, 1518 is made from a length of nitinol tubing which is cut or machined and heat treated as discussed below. Further, alternative materials such as stainless steel or elgiloy could also be used.

As shown in FIG. 6b, the tines 18a, 118a, 218a, 418a, 518a, 618a, 718a, 1318a can be tapered toward the free end (unnumbered), however, it is not essential to have tapered tines. The advantage to this configuration is that tapered tines 18a, 118a, 218a, 418a, 518a, 618a, 718a, 1318a, 1418a, 1518a would have increased buckling at the attached end (unnumbered) as well as improved trauma characteristics at the free end (unnumbered). It is additionally contemplated to form loops 818a having an other than parallel configuration throughout their length to impart special force characteristics.

Following formation of the various embodiments of the anchor mechanism 18, 118, 218, 418, 518, 618, 718, 818, 1318, 1418, 1518 and braid 910, 1010, 1110, 1210 as described above, it is necessary to process at least the tines 18a, 118a, 218a, 418a, 518a, 618a, 718a, 1318a, 1418a, 1518a, loops 818a and braid 910, 1010, 1110, 1210 to have the proper shape upon deployment to subcutaneously anchor the anchoring device within the patient. It is similarly necessary to process the shape of the lock spring 29, 129, 229 to have a shape extending away from the length of the control rod 18b, 118b, 218b, the function of which is explained in detail below. The shape training process also imparts superelasticity, as explained in detail below, to at least the tines 18a, 118a, 218a, 418a, 518a, 618a, 718a, 1318a, 1418a, 1518a, loops 818a and braid 910, 1010, 1110, 1210 assuming they are made out of nitinol. When the integral anchor mechanism 18, 418, 518, 618, 718, 818, 1318, 1418, 1518 is cut or machined from its source material and when the welded anchor mechanisms 118, 218 are assembled, the tines 18a, 118a, 218a, 418a, 518a, 618a, 718a, 1318a, 1418a, 1518a, loops 818a, braid 910, 1010, 1110, 1210 and lock spring 29, 129, 229 are placed in a forming jig (not shown) which holds the tines 18a, 118a, 218a, 418a, 518a, 618a, 718a, 1318a, 1418a, 1518a, loops 818a, braid 910, 1010, 1110, 1210 and lock spring 29, 129, 229 in the position they will eventually be trained into. In the embodiment shown in FIG. 21 the spring portion 722 is simultaneously placed into a separate area of the forming portion (not shown). In a preferred embodiment, the tines 18a, 118a, 218a, 418a, 518a, 618a, 718a, 1318a, 1418a, 1518a, loops 818a, spring portion 722, lock spring 29, 129, 229 and braid 910, 1010, 1110, 1210 are subjected to a temperature of 500 degrees C. plus or minus 100 degrees C. for less than thirty minutes, depending on the alloy chemistry, dimensions, fixturing and heat source. Different heat sources include salt bath, hot air torch and oven. A heavier and larger fixture will take a longer length of heat treatment time. Following heat treatment, the heated anchor mechanism 18, 118, 218, 418, 518, 618, 718, 818, 1318, 1418, 1518 and braid 910, 1010, 1110, 1210 should be quickly cooled as by an air fan. Making the anchor mechanism 18, 118, 218, 418, 518, 618, 718, 818, 1318, 1418, 1518 and braid 910, 1010, 1110, 1210 from non-superelastic materials such as stainless steel, spring steel or carbon fiber is also contemplated by and therefore within the scope of the invention.

In a preferred embodiment, the anchor mechanism 18, 118, 218, 418, 518, 618, 718, 818, 1318, 1418, 1518 and braid 918, 1018, 1118, 1218 is formed from nitinol wire, sheet or tubing that has been processed to exhibit superelasticity at somewhere below human body temperature (around 37 degrees C.). The invention also contemplates forming the anchor mechanism 18, 118, 218, 418, 518, 618, 718, 818, 1318, 1418, 1518 and braid 918, 1018, 1118, 1218 from nitinol processed to exhibit thermal shape memory characteristics at human body temperature. Nitinol is an approximate stoichiometric alloy of nickel and titanium; however, other elements such as vanadium are sometimes added in small amounts to alter the mechanical characteristics of the alloy. Chemical composition and processing history primarily determine the particular mechanical properties of a shape memory/superelastic metallic alloy. In general, such an alloy will exist in either one or the other, or combinations of two crystallographic phases. Austenite is the parent crystallographic phase and exists at higher temperatures. Martensite is the other phase and is formed by either subjecting the alloy to lower temperatures or by placing mechanical or physical stress on the alloy while it is in the austenitic phase. Transition temperatures between these two phases can be experimentally determined for a particular alloy. Processing history includes high temperature annealing as well as low temperature forming and deformation. Following standard material and processing specifications, the transitional temperatures that define the alloy's mechanical characteristics are predictable and controllable. Standard transitional temperature designations are given as: $M_s$ for the start of the transition to the martensitic phase, $M_f$ for completion of the transition to martensite, $A_s$ for the start of the transition to the austenitic phase, and $A_f$ for the completed transition to austenite.

Superelasticity is based on phase transition from austenite to martensite. Mechanically induced phase transition from austenite to martensite occurs when the alloy temperature is above $A_f$ and a physical restraint is applied to the alloy. As long as the restraint is in place, the portion of the alloy receiving the stress reverts to the martensitic phase, which remains as long as the stress is maintained. Unless the shape recovery limits are exceeded, when the restraint is removed and the stress is released the alloy returns to its original austenitic phase and shape as long as the temperature is maintained above $A_f$. Thus, when the austenitic, trained shape of the alloy is deformed and held by stress in a new shape, a certain amount of force is exerted by the alloy against the restraint as it resists the new, untrained shape.

The thermal shape memory effect of these alloys has been known much longer than superelasticity. Thermal shape memory occurs as the result of a piece of shape memory alloy metal being deformed while in the lower temperature martensitic phase and then being reheated to a temperature somewhere above $A_s$ which causes the alloy to reform in the austenitic phase. When the crystallographic nature of the alloy is completely austenitic, the alloy's shape returns to the previously trained shape. Shape memory training occurs when a thermal shape memory/superelastic metallic alloy is annealed (heat treated) while restrained in a certain shape. The trained shape will then be maintained unless it is deformed while in the low temperature martensitic phase. Upon reheating the alloy to the austenitic phase, the original shape, which was "learned" in the annealing process, will be "remembered" and returned to. Thus, temperature change is one way of controlling the crystallographic phase of a shape memory/superelastic metallic alloy.

One practical advantage of a shape memory/superelastic alloy over non-superelastic materials is that it can be deformed to a far greater degree without taking a permanent set or kink. In the case of superelastic alloys (i.e., alloys processed to exhibit superelasticity at body temperature), assuming the alloy is above the $A_f$ temperature, removal of the restraint alone is sufficient to resume the original, trained shape. When the alloy is processed to have shape memory characteristics, the martensitic phase alloy need only be subjected to temperatures somewhere above $A_f$ and the alloy will eventually return to its original, trained shape. It is also possible to use a restraint in conjunction with alloys trained to exhibit thermal shape memory characteristics.

Thus, when an anchor mechanism 18, 118, 218, 418, 518, 618, 718, 818, 1318, 1418, 1518 and braid 910, 1010, 1110, 1210 made of nitinol is processed to exhibit superelastic characteristics at somewhere below human body temperature, it uses superelasticity in two different ways. First, superelasticity (stress-induced martensite) allows the anchor mechanism 18, 118, 218, 418, 518, 618, 718, 818, 1318 to be repeatedly deformed to a degree sufficient to enable it to be loaded into the chamber 14a, 114a, 414a, 514a, 614a, 714a, 814a, 1314a of the anchor sleeve 14, 114, 414, 514, 614, 714, 814, 1314 without taking a permanent set or kink. In the embodiments shown in FIGS. 24-29a, the braid 910, 1010, 1110, 1210 is able to be repeatedly deformed without taking a set or kink. While the anchor mechanism 18, 118, 218, 418, 518, 618, 718, 818, 1318, 1418, 1518 is restrained by the chamber 14a, 114a, 414a, 514a, 614a, 714a, 814a, 1314a, retaining band 1412 or outer sheath 1514, assuming the anchor mechanism 18, 118, 218, 418, 518, 618, 718, 818, 1318, 1418, 1518 is maintained at a temperature above $A_f$, the tines 18a, 118a, 218a, 418a, 518a, 618a, 718a, 1318a, 1418a, 1518a and loops 818a contacting the inner walls (unnumbered) of the chamber 14a, 114a, 414a, 514a, 614a, 714a, 814a, 1314a, retaining band 1412 or outer sheath 1514 are exerting an amount of force against the chamber 14a, 114a, 414a, 514a, 614a, 714a, 814a, 1314a, retaining band 1412 or outer sheath 1514 due to the formation of stress-induced martensite. The force exerted by the tines 18a, 118a, 218a, 418a, 518a, 618a, 718a, 1318a, 1418a, 1518a and loops 818a, against the chamber 14a, 114a 414a, 514a, 614a, 714a, 814a, 1314a, retaining band 1412 or outer sheath 1514 thus helps the anchor mechanism 18, 118, 218, 418, 518, 618, 718, 818, 1318, 1418, 1518 to remain in the undeployed configuration until the physician determines the retention device 10, 100, 400, 500, 600, 700, 800, 1300, 1400, 1500 and coupled medical device is properly introduced into the patient.

Following proper introduction, in the embodiments shown in FIGS. 1-17 the tines 18a, 118a, 218a, 418a are then controllably and gently deployed through the ports 20, 120, 420 to secure the catheter 12, 112, 412 or sheath introducer (not shown) in place below the skin for the duration of the treatment period. In the embodiments shown in FIGS. 18-22a and 30-35 the physician receives the retention device 500, 600, 700, 800, 1300 in the undeployed configuration and removes the key 534, 634, 734, 834, 1334 from the key aperture 536, 636, 736, 836, 1336 thus causing proximal movement of the anchor mechanism 518, 618, 718, 818, 1318 and controllable, gentle and simultaneous deployment of the tines 518a, 618a, 718a, 1318a and loops 818a through the ports 520, 620, 720, 820, 1320, which is biased by the spring 522, 622, 722, 822, 1322 into the default, deployed configuration.

The second way the retention device 10, 100, 200, 400, 500, 600, 700, 800, 900, 1000, 1100, 1200, 1300, 1400, 1500 uses superelasticity is that the processing of nitinol can be varied to program a desired amount of release force into the tines 18a, 118a, 218a, 418a, 518a, 618a, 718a, 1318a, 1418a, 1518a, loops 818a and braid 910, 1010, 1110, 1210. This is advantageous because certain uses of the retention device 10, 100, 200, 400, 500, 600, 700, 800, 900, 1000, 1100, 1200, 1300, 1400, 1500 may require a stronger pull strength than other uses. By programming the superelastic nitinol to a greater or lesser amount of strength, tines 18a, 118a, 218a, 418a, 518a, 618a, 718a, 1318a, 1418a, 1518a, loops 818a and braid 910, 1010, 1110, 1210 can be programmed that will release at a particular pull strength, rather than be painfully ripped out of the patient.

When the anchor mechanism 18, 118, 218, 418, 518, 618, 718, 818, 1318, 1418, 1518 and braid 910, 1010, 1110, 1210 is formed to exhibit thermal shape memory characteristics at body temperature, the $A_f$ is programmed into the alloy to be somewhere below human body temperature. The $A_s$ of the anchor mechanism 18, 118, 218, 418, 518, 618, 718, 818, 1318, 1418, 1518 and braid 910, 1010, 1110, 1210 is somewhere below room temperature prior to introduction into the patient's body. Alternatively, the anchor mechanism 18, 118, 218, 418, 518, 618, 718, 818, 1318, 1418, 1518 and braid 910, 1010, 1110, 1210 (and consequently the whole retention device 10, 100, 400, 500, 600, 700, 800, 900, 1000, 1100, 1200, 1300, 1400, 1500) is cooled to a temperature below $M_f$ to place the anchor mechanism 18, 118, 218, 418, 518, 618, 718, 818, 1318, 1418, 1518 and braid 910, 1010, 1110, 1210 in the martensitic phase prior to introduction into the patient's body. When the retention device 10, 100, 400, 500, 600, 700, 800, 900, 1000, 1100, 1200, 1300, 1400, 1500 is being introduced into the body (not shown), means must be used to maintain the temperature of the retention device 10, 100, 400, 500, 600, 700, 800, 1000, 1100, 1200, 1300, 1400, 1500 below $A_s$. Typically, a cold saline drip (not shown) is maintained through the chamber 14a, 114a, 414a, 514a, 614a, 714a, 814a, 1314a, the retention device 1400, 1500 or over the braid 910, 1010, 1110, 1210 during the introduction procedure. Following introduction of the retention device 10, 100, 400, 500, 600, 700, 800, 900, 1000, 1100, 1200, 1300, 1400, 1500 and coupled medical device at the treatment site within the patient's body, the tines 18a, 118a, 218a, 418a, 518a, 618a, 718a, 1318a, 1418a, 1518a and loops 818a are advanced from the ports 20, 120, 420, 520, 620, 720, 820, 1320, 1520 of the anchor sleeve 14, 114, 414, 514, 614, 714, 814, 1314, outer sheath 1514 or released from the retaining band 1412 whereupon it is exposed to body temperature, which is above the $A_f$ of the alloy. Exposure to body temperature raises the temperature of the alloy to a point where the tines 18a, 118a, 218a, 418a, 518a, 618a, 718a, 1318a, 1418a, 1518a loops 818a and braid 910, 1010, 1110, 1210 are in the austenitic phase, returning the tines 18a, 118a, 218a, 418a, 518a, 618a, 718a, 1318a, 1418a, 1518a, loops 818a and braid 910, 1010, 1110, 1210 toward their original, trained shape. Because the tines 18*a*, 118*a*, 218*a*, 418*a*, 518*a*, 618*a*, 718*a*, 1318*a*, 1418*a*, 1518*a*, loops 818*a* and braid 910, 1010, 1110, 1210 are deployed beneath the patient's skin S, they may be somewhat restrained by anatomical space limitations and therefore may not fully assume the trained shape.

Use

Using the retention device 10, 100, 400, 500, 600, 700, 800, 900, 1000, 1100, 1200, 1300, 1400, 1500 requires the physician to create an external incision or skin puncture proximate the internal area to be accessed. In some cases it is also be necessary to create an incision by a scalpel or needle in an underlying vessel V or proximal an anatomical site to facilitate placement of retention device 10, 100, 400, 500, 600, 700, 800, 900, 1000, 1100, 1200, 1300, 1400, 1500 and coupled medical device (not shown). The embodiments of the retention device 10, 400 shown in FIGS. 2-5 and 14-17 have the anchor sleeve 114, 414 directly attached to a catheter 12, 412. The embodiment of the retention device 10 shown in FIGS. 1 and 10-13 show the anchor sleeve 14 attached to an introducer sheath 16. In this embodiment of the retention device 10, following introduction into a patient, a separate catheter 12 is navigated through the lumen 16*a* of the introducer sheath 16. The catheter 12, 112, 412 when inserted serves as a direct conduit for infusing therapeutic solutions, draining body fluids or delivering mechanical devices to an anatomical site. A needle (not shown) or guidewire (not shown) or dilator/sheath/guiding catheter system (not shown) is used to access the underlying vessel V or an anatomical site, the interior of which is then entered. The retention device 10, 100, 400, 500, 600, 700, 800, 900, 1000, 1100, 1200, 1300, 1400, 1500 and coupled medical device is then adjusted as shown in FIGS. 1 and 36 to the desired anatomical depth.

Following depth adjustment of the retention device 10, 100, 400, 500, 600, 700, 800, 900, 1000, 1100, 1200, 1300, 1400, 1500, in the embodiments shown in FIGS. 1-17, the physician moves the control rod 18*b*, 118*b*, 218*b*, 418*b* in a proximal direction by grasping and sliding the handle 40 which controllably, gently and simultaneously moves tines 18*a*, 118*a* 218*a*, 418*a* in a proximal direction. The control rod 18*b*, 118*b*, 218*b*, 418*b* is prevented from excess proximal movement by the length of the tines 18*a*, 118*a*, 218*a*, 418*a* and locked into the desired position by the lock spring 29 rising into the internal recess 32 in the chamber 14*a*, 114*a*, 414*a*. Moving the control rod 18*b*, 118*b*, 218*b*, 418*b* proximally thus results in the tines 18*a*, 118*a* 218*a*, 418*a* puncturing the membranes 22 and thus exiting the anchor sleeve 14, 114, 414 through ports 20, 120, 420. By means of various lock positions available to the physician as a result of the lock system, the tines 18*a*, 118*a* 218*a*, 418*a* can be extended to the degree desired by the physician. Thus, the tines 18*a*, 118*a* 218*a*, 418*a* can be extended so as to define a partial arc as shown in FIGS. 1, 2*b*, 6-9, 11, 13 and 15. Alternatively, if the tines 18*a*, 118*a* 218*a*, 418*a* have been trained to assume a longer circumference, they can be more fully extended to assume a semi-circular (not shown) or even fully circular (not shown), shape. An advantage to all embodiments of the present invention herein is that due to controllable and gentle deployment, the retention device is much less likely to cause internal trauma in the subcutaneous environments it is used in.

In the embodiments of the retention device 500, 600, 700, 800, 1300 shown in FIGS. 18-23 and 30-31, in a preferred embodiment as discussed above, the physician receives the retention device 500, 600, 700, 800, 1300 in the undeployed configuration, with the seals 521, 621, 721, 821, 1321 intact and with the key 534, 634, 734, 834, 1334 inserted in the key aperture 536, 636, 736, 836, 1336 which is held in place by the locking mechanism. Upon reaching the desired anatomical depth the physician unlocks and removes the key 534, 634, 734, 834, 1334 which results in the tines 518*a*, 618*a*, 718*a*, 1318*a* and loops 818*a* breaking the seals 521, 621, 721, 821, 1321 thus controllably and gently deploying the retention device 500, 600, 700, 800, 1300 for the duration of the treatment period.

In the embodiments shown in FIGS. 24-29*a* the retention device 900, 1000, 1100, 1200 can surround a medical device which defines a lumen (unnumbered) which provides communication between the interior and exterior of a patient's body. It is also contemplated (not shown) to couple the retention device 900, 1000, 1100, 1200 to a medical device (not shown) in a manner which does not completely surround the medical device (not shown). Following introduction into the patient when the retention device 900, 1000, 1100, 1200 is in the undeployed configuration as shown in FIGS. 25, 25*a*, and 29 and upon reaching the desired depth the physician slides the outer sheath 914, 1014, 1114, 1214 in a direction so that the braid 910, 1010, 1110, 1210 assumes the deployed configuration as shown in FIGS. 24, 26, 27 and 28. The retention device 900, 1000, 1100, 1200 is provided with at least one locking tab 916, 1016, 1116, 1216 which serves to maintain the retention device 900, 1000, 1100, 1200 in the deployed configuration for the duration of treatment. It is also contemplated to provide a series (not shown) of locking tabs 916, 1016, 1116, 1216 extending along the length of the retention device which would allow the physician varying degrees of deployment.

In the embodiment of the retention device 1400 shown in FIGS. 32-33 the physician receives the coupled medical device and retention device 1400 in the undeployed configuration. The physician then creates an incision and inserts the retention device 1400 and coupled medical device. Upon reaching the desired anatomical depth the physician slides the actuator 1420 in the direction indicated in FIG. 32 which is attached to the anchor mechanism by a control member 1419. The actuator 1420 is attached to the anchor mechanism 1418 which results in the tines 1418*a* sliding in a direction allowing their escape from the retaining band 1412 thus deploying the retention device 1400 for the duration of the treatment period.

In the embodiment of the retention device 1500 shown in FIGS. 34-35 the physician receives the coupled medical device and retention device 1500 in the undeployed configuration. The physician then creates an incision and inserts the retention device 1500 and coupled medical device. Upon reaching the desired anatomical depth the physician slides the outer sheath 1514 in the direction indicated in FIG. 35. This results in the tine(s) 1518*a* escaping through the port(s) 1520 allowing them to at least partially assume their unrestrained, trained shape thus deploying the retention device 1400 for the duration of the treatment period.

The embodiments of the retention device 10, 100, 400, 500, 600, 700, 800, 900, 1000, 1100, 1200 1300, 1400, 1500 are preferably integrally attached to a medical device such as a catheter, sheath introducer, feeding tube, ostomy bag, pacing lead or other device intended for temporary but extended implantation in a patient. In another embodiment, the retention device 10, 100, 400, 500, 600, 700, 800, 900, 1000, 1100, 1200, 1300, 1400, 1500 is contemplated to be separately attachable to the above listed medical devices by such means as (but not limited to) press fit, adhesives, hook and loop fastener material, snaps, retaining rings, thermal melting techniques, sonic welding, crimping, heat shrink, mechanical fasteners, or a sheath introducer.

Removing the retention device 10, 100, 400 from the patient involves unlocking the lock system by depressing the lock spring 29 from the recess 32 with the key 34 and moving the control rod 18b, 118b, 218b, 418b via the handle 40 in a distal direction. This results in the tines 18a, 118a 218a, 418a simultaneously moving in a distal direction whereby the tines 18a, 118a 218a, 418a reenter the anchor sleeve 14, 114, 414 through the ports 20, 120, 420 whereby the retention device 10, 100, 400 is removed from the patient following completion of the course of treatment.

Removing the retention device 500, 600, 700, 800, 1300 from the patient at the termination of treatment, the physician reverses the introduction procedure by re-inserting the key 534, 634, 734, 834, 1334 into the respective key aperture 536, 636, 736, 836, 1336. This results in the anchor mechanism 518, 618, 718, 818, 1318 and tines 518a, 618a, 718a, 1318a or loops 818a simultaneously retracting into the chamber 514a, 614a, 714a, 814a, 1314a which allows removal of the retention device 500, 600, 700, 800, 1300 from the patient.

Removing the retention device 900, 1000, 1100, 1200 from the patient at the termination of treatment requires the physician to first unlock the locking tab 916, 1016, 1116, 1216. The physician next moves the outer sheath 914, 1014, 1114, 1214 in a direction allowing the braid 910, 1010, 1110, 1210 to resume its undeployed configuration, allowing removal of the retention device 900, 1000, 1100, 1200 and coupled medical device (not shown).

Removing the retention device 1400 from the patient requires the physician to re-insert the actuator 1420 into the actuator groove 1414 and exert an amount of force necessary to slide the anchor mechanism 1418 into the position shown in FIG. 32. This simultaneously restrains the tine(s) 1418 and thus, the retention device 1400 is returned to its undeployed configuration. The physician is then able to remove the retention device 1400 and coupled medical device from the patient.

Removing the retention device 1500 from the patient requires the physician to re-slide the outer sheath 1514 into the position shown in FIG. 34. This simultaneously restrains the tine(s) 1418 and thus, the retention device 1500 is returned to its undeployed configuration. The physician is then able to remove the retention device 1500 and coupled medical device from the patient.

What is claimed is:

1. A method for securing a catheter relative to a skin opening that is occupied by the catheter, the method comprising:
    inserting a distal portion of a catheter through an opening in a skin layer and into a targeted body site;
    advancing first and second flexible anchors of a catheter anchor device through the same opening in the skin layer and into a subcutaneous region under the skin layer, wherein the catheter anchor device comprises:
        a catheter retainer body including a longitudinal channel configured to releasably engage with an outer surface of an external portion of the catheter; and
        an anchor assembly contacting the retainer body and being spaced apart from the channel of the retainer body, the anchor assembly including: a longitudinal extender apparatus secured to the catheter retainer body, and said first and second flexible anchors extending outwardly away from a distal region of the longitudinal extender apparatus, each of the first and second flexible anchors terminating at a non-sharp tip, wherein the first and second flexible anchors are movable from a first position to a subcutaneously deployed position in which the first and second flexible anchors extend outwardly away from one another in generally opposite directions and are configured to engage tissue along an underside of the skin layer; and
    maintaining the external portion of the catheter in securement with the catheter retainer body while the non-sharp tips of the first and second flexible anchors reside within the subcutaneous region under the skin layer and while the distal portion of the catheter extends into the targeted body site.

2. The method of claim 1, further comprising withdrawing the first and second flexible anchors of the catheter anchor device from the subcutaneous region and out through the same opening in the skin layer.

3. The method of claim 2, further comprising adjusting the first and second flexible anchors of the catheter anchor device to a withdrawal position that is different from the subcutaneously deployed orientation during withdrawal from the subcutaneous region and out through the same opening in the skin layer.

4. The method of claim 1, wherein the first and second flexible anchors are capable of repeatedly moving between the first position in which the first and second flexible anchors are arranged for insertion through the opening in the skin layer and the subcutaneously deployed position in which the first and second flexible anchors extend outwardly away from one another in generally opposite directions.

5. The method of claim 1, wherein when the first and second flexible anchors are positioned in the subcutaneously deployed position, a space between the tips of the first and second flexible anchors is greater than a space between the tips of the first flexible and second flexible anchors when the first and second flexible anchors are positioned in the first position.

6. The method of claim 1, further comprising maintaining the first and second flexible anchors in the subcutaneously deployed position using a locking system of the catheter anchor device.

7. The method of claim 1, further comprising disposing the catheter anchor device on an exterior of the skin layer proximate to the opening in the skin layer.

8. The method of claim 7, wherein the anchor device is disposed on the skin layer proximate to an underlying vessel, and wherein the distal portion of the catheter is inserted through the opening in the skin layer and into the underlying vessel.

9. The method of claim 1, wherein the first and second flexible anchors comprise a material selected from the group consisting of stainless steel and nitinol.

10. The method of claim 1, wherein the anchor assembly is movable relative to the catheter retainer body.

11. The method of claim 1, wherein the longitudinal extender apparatus comprises a rod.

12. The method of claim 11, further comprising actuating the rod relative to the catheter retainer body so as to flexibly adjust the first and second flexible anchors from the first position to the subcutaneously deployed position.

13. The method of claim 1, wherein the non-sharp tip of each of the first and second flexible anchors comprises a dull or rounded tip.

14. The method of claim 1, wherein the first flexible anchor includes a first lengthwise convexly flexible portion extending toward the tip of the first flexible anchor such that the first lengthwise convexly flexible portion bows toward the catheter retainer body.

15. The method of claim 14, wherein the second flexible anchor includes a second lengthwise convexly flexible portion extending toward the free end of the second flexible anchor such that the second lengthwise convexly flexible portion bows toward the retainer body.

16. The method of claim 15, wherein the first lengthwise convexly flexible portion of the first flexible anchor and the second lengthwise convexly flexible portion of the second flexible anchor face toward the underside of the skin layer when the first and second flexible anchors are subcutaneously deployed.

17. The method of claim 1, wherein each of the first and second flexible anchors is deployable from a corresponding port along an exterior of the catheter anchor device.

\* \* \* \* \*

UNITED STATES PATENT AND TRADEMARK OFFICE
CERTIFICATE OF CORRECTION

Page 1 of 1

PATENT NO.        : 9,884,168 B2
APPLICATION NO.   : 14/946452
DATED             : February 6, 2018
INVENTOR(S)       : Michael S. Rosenberg and Timothy J. Claude It is certified that error appears in the above-identified patent and that said Letters Patent is hereby corrected as shown below:

On the Title Page

Page 2, item (63), Column 1, Line 6 delete "/US13/" and insert --/US03/--, therefor.

Signed and Sealed this
Third Day of July, 2018

Andrei Iancu
*Director of the United States Patent and Trademark Office*